United States Patent
Ohara et al.

(10) Patent No.: US 9,850,317 B2
(45) Date of Patent: Dec. 26, 2017

(54) ANTI-DOG IGE MONOCLONAL ANTIBODY, AND LIGHT-CHAIN VARIABLE REGION AND HEAVY-CHAIN VARIABLE REGION OF ANTI-DOG IGE MONOCLONAL ANTIBODY

(71) Applicants: KAZUSA DNA RESEARCH INSTITUTE, Kisarazu-shi, Chiba (JP); ANIMAL ALLERGY CLINICAL LABORATORIES INC., Sagamihara-shi, Kanagawa (JP); NIPPON ZENYAKU KOGYO CO., LTD., Koriyama-shi, Fukushima (JP)

(72) Inventors: Osamu Ohara, Kisarazu (JP); Takahiro Nagase, Kisarazu (JP); Yoshihiro Yamaguchi, Kisarazu (JP); Reiko Ohara, Kisarazu (JP); Kenichi Masuda, Sagamihara (JP); Toshihiro Tsukui, Koriyama (JP)

(73) Assignees: KAZUSA DNA RESEARCH INSTITUTE, Kisarazu-Shi, Chiba (JP); ANIMAL ALLERGY CLINICAL LABORATORIES INC., Sagamihara-Shi, Kanagawa (JP); NIPPON ZENYAKU KOGYO CO., LTD., Koriyama-Shi, Fukushima (JP)

( * ) Notice: Subject to any disclaimer, the term of this patent is extended or adjusted under 35 U.S.C. 154(b) by 0 days.

(21) Appl. No.: 14/778,452

(22) PCT Filed: Mar. 17, 2014

(86) PCT No.: PCT/JP2014/057190
§ 371 (c)(1),
(2) Date: Sep. 18, 2015

(87) PCT Pub. No.: WO2014/148444
PCT Pub. Date: Sep. 25, 2014

(65) Prior Publication Data
US 2016/0272728 A1 Sep. 22, 2016

(30) Foreign Application Priority Data
Mar. 19, 2013 (JP) ................................ 2013-057015

(51) Int. Cl.
*C07K 16/42* (2006.01)
*C12N 15/85* (2006.01)
*G01N 33/577* (2006.01)
*G01N 33/68* (2006.01)

(52) U.S. Cl.
CPC ...... *C07K 16/4291* (2013.01); *C12N 15/8509* (2013.01); *G01N 33/577* (2013.01); *G01N 33/6854* (2013.01); *A01K 2217/052* (2013.01); *A01K 2227/706* (2013.01); *A01K 2267/01* (2013.01); *C07K 2317/14* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/624* (2013.01); *C07K 2317/626* (2013.01); *C07K 2319/21* (2013.01); *C12N 2015/8518* (2013.01)

(58) Field of Classification Search
None
See application file for complete search history.

(56) References Cited

U.S. PATENT DOCUMENTS

| 6,060,326 | A   | * | 5/2000 | Frank  | G01N 33/566 435/6.1 |
| 6,504,013 | B1  | * | 1/2003 | Lawton | C07K 16/4291 424/141.1 |
| 8,716,031 | B2  | * | 5/2014 | Masuda | C07K 16/4291 435/337 |
| 2011/0111529 | A1 |   | 5/2011 | Masuda et al. | |

FOREIGN PATENT DOCUMENTS

| JP | 2006-151880 A | 6/2006 |
| WO | WO 2009/139378 A1 | 11/2009 |

OTHER PUBLICATIONS

Janeway et al., Immunobiology, 3$^{rd}$ edition, 1997, Garland publications, 3:1-3:11.*
Rudikoff et al., Proc Natl Acad Sci U S A. Mar. 1982;79(6):1979-83.*
Portolano et al., J Immunol. Feb. 1, 1993;150(3):880-7.*
Fundamental Immunology, William E. Paul, M.D. ed., 3d ed. 1993, p. 242.*
European Search Report for Appl. No. 14769566.2 dated Nov. 17, 2016.
Peng, Z., et al, "Purification and Identification of Polyclonal IgE Antibodies from Ragweed-Sensitized Dog Sera," Int Arch Allergy Immunol, 1993, vol. 102, pp. 176-184.
Deboer et al., "Production and characterization of mouse monoclonal antibodies directed against canine IgE and IgG", Veterinary Immunology and Immunopathology, 1993, vol. 37, pp. 183-199.

(Continued)

*Primary Examiner* — Michael Szperka
(74) *Attorney, Agent, or Firm* — Birch, Stewart, Kolasch & Birch, LLP

(57) ABSTRACT

Problem to be Solved: The present invention is intended to provide a polynucleotide encoding the light-chain variable region and the heavy-chain variable region of an anti-dog IgE antibody; and an anti-dog IgE antibody containing these variable regions.

Solution: The present invention is DNA encoding a heavy-chain variable region consisting of the amino acid sequence represented by SEQ ID NO: 2 or 6 and DNA encoding a light-chain variable region consisting of the amino acid sequence represented by SEQ ID NO: 4 or 8, and an anti-dog IgE monoclonal antibody which binds to dog IgE, containing these variable regions or a functional fragment thereof which binds to dog IgE.

24 Claims, 20 Drawing Sheets

(56) References Cited

OTHER PUBLICATIONS

Derer et al., "Monoclonal anti-IgE antibodies in the diagnosis of dog allergy", Veterinary Dermatology: an International Journal, 1998, vol. 9, No. 3, pp. 215-221. (with translation).
International Search Report, issued in PCT/JP2014/057190, dated Jun. 17, 2014.
Written Opinion of the International Searching Authority, issued in PCT/JP2014/057190, dated Jun. 17, 2014.

* cited by examiner

A

B

C

D

E

F

A

X1 KCR clone

| Primer No. | Primer name | Sequence | SEQ ID NO: | Nucleotide length |
|---|---|---|---|---|
| Primer 1 | X1_IGH2ver2_F | TCGTGGATGTGCTGATACAACCAGC | SEQ ID NO:21 | 25 |
| Primer 2 | X1_IGH2ver2_R | GGGTGCTTATTTACACAAGGCAAGG | SEQ ID NO:22 | 26 |
| Primer 3 | ratIGH_X1_5' | ATGGACAGGCTTACTTCGTCA | SEQ ID NO:23 | 21 |
| Primer 4 | X1_IgG2CH1_Rev | GGTGTATCACCACATCCAG | SEQ ID NO:24 | 20 |
| Primer 5 | X1_IgG2CH3end_Rev | TTTACCGGCAGGCCGGGAG | SEQ ID NO:25 | 19 |
| Primer 6 | ratIGH_X1_5'Tag | ATAACGGCGATCGGATGGACAGGCTTACTTCGTCA | SEQ ID NO:26 | 34 |
| Primer 7 | X1_IgG2CH3end_RevTAG | CTAATGATGGTGATGGTGATGTTACCCGGAGGCCGGGAG | SEQ ID NO:27 | 40 |
| Primer 8 | muIGH_H5_5' | ATGGAATGGAGCTGGGATCTTC | SEQ ID NO:28 | 22 |
| Primer 9 | H5_IgHVend_ratCH1Tag | GGGCTGTTGTTGGGCTGCAGAGACAGTGACCAGAG | SEQ ID NO:29 | 36 |
| Primer 10 | X1_IgG2CH1_Fw | GCCCAAAACAACAGCCCCATC | SEQ ID NO:30 | 20 |
| Primer 11 | muIGH_H5_5'Tag | ATAACGGCGATGGCATGGAATGGAGCTGGATCTTC | SEQ ID NO:31 | 35 |
| Primer 12 | X1_IGK2ver2_F | AGGCACCAAGCTGGAATTGAAACGG | SEQ ID NO:32 | 25 |
| Primer 13 | X1_IGK2ver2_R | GCAGGTGGCACCTCAGGACCTTTGG | SEQ ID NO:33 | 25 |
| Primer 14 | muIGK_H5_5' | ATGAAGTTGCCTGTTAGGCTG | SEQ ID NO:34 | 21 |
| Primer 15 | H5_IgKVend_ratCHTag | GTGCAGCATCAGCCCGTTTGATTCCAGCTTGGTGC | SEQ ID NO:35 | 36 |
| Primer 16 | ratIGK_X1_5' | ATGATGATTCCTGCCCAGTC | SEQ ID NO:36 | 21 |
| Primer 17 | X1_IgKVend_CHTag | GTGCAGCATCAGCCCGTTTCAATTCCAGCTTGGTG | SEQ ID NO:37 | 35 |
| Primer 18 | X1_IgKCH_Fw | CGGGCTGATGCTGCACCAAC | SEQ ID NO:38 | 20 |
| Primer 19 | X1_IgKCH_Rev | ACACTCATTCGTGTTGAAGCT | SEQ ID NO:39 | 21 |
| Primer 20 | muIGK_H5_5'Tag | ATAACGGCGATGGCATGAAGTTGCCTGTGTAGGCTG | SEQ ID NO:40 | 34 |
| Primer 21 | X1_IgKCH_RevTag | CTAATGATGGTGATGGTGATGAAGTTGCTGATGACACTCATTCCTGTGTTGAAGCT | SEQ ID NO:41 | 42 |
| Primer 22 | ratIGK_X1_5'Tag | ATAACGGCGATGCATGGCATGATGATTCCTGCCCAGTT | SEQ ID NO:42 | 34 |
| Primer 23 | RatCRHCH5_BM030 | CCCGAATTCAGCATGGTCGAGGCTGGATCTT | SEQ ID NO:43 | 33 |
| Primer 24 | RatCR_rev | CCCTCTAGAGTAATGATGGTGATGGTGAT | SEQ ID NO:44 | 30 |
| Primer 25 | RatCRKCH5_BM030 | CCCGAATTCACCATGACGATGAAGTTGCCTGTTAGGCT | SEQ ID NO:45 | 33 |
| Primer 26 | RatCRHCX1_BM030 | CCCGAATTCACCATGGACAGGCTTACTTCCTG | SEQ ID NO:46 | 33 |
| Primer 27 | RatCRKCX1_BM030 | CCCGAATTCACCATGATGATTCCTGCCCAGTT | SEQ ID NO:47 | 33 |
| Primer 28 | RatCRHCH5dsp_BM030 | CGGGAATTCAGATGTCAGGCTGCAGGAGAGTG | SEQ ID NO:48 | 30 |
| Primer 29 | RatCRKCH5dsp_BM030 | CCGGAATTCGATGTGTGATGACGCAAAC | SEQ ID NO:49 | 30 |
| Primer 30 | RatCRHCX1dsp_BM030 | CCGGAATTCAGGTTACTCGAAAGAGTG | SEQ ID NO:50 | 30 |
| Primer 31 | RatCRKCX1dsp_BM030 | CCCGAATTCGTGTTGATGACCAGAC | SEQ ID NO:51 | 30 |

ANTI-DOG IGE MONOCLONAL ANTIBODY, AND LIGHT-CHAIN VARIABLE REGION AND HEAVY-CHAIN VARIABLE REGION OF ANTI-DOG IGE MONOCLONAL ANTIBODY

TECHNICAL FIELD

The present invention relates to a heavy-chain variable region or a light-chain variable region of an antibody specifically binding to dog IgE and polynucleotides encoding these regions. The present invention further relates to a monoclonal antibody containing the heavy-chain variable region and the light-chain variable region.

BACKGROUND ART

IgE is responsible for allergy, particularly type I allergy. In recent years, allergic diseases have increased in dogs raised as pet animals, like humans.

Probable methods for treating type I allergy include the use of a compound which binds to IgE in serum and suppressing the binding of IgE to mast cells, and examples thereof suggested include the use of an antibody which binds to the Fc region of IgE (see Patent Literature 1).

CITATION LIST

Patent Literature

Patent Literature 1: JP Patent Publication (Kokai) No. 2006-151880

SUMMARY OF INVENTION

Technical Problem

An object of the present invention is to provide a heavy-chain variable region or a light-chain variable region of an anti-dog IgE antibody and polynucleotides encoding these regions. Another object of the present invention is to provide an anti-dog IgE antibody containing these variable regions.

Solution to Problem

The present inventors have conducted intensive studies on a method for preparing a dog IgE monoclonal antibody, and obtained a hybridoma producing a monoclonal antibody recognizing and binding to dog IgE. In addition, the inventors have cloned DNA encoding a heavy-chain variable region of an anti-dog IgE antibody and DNA encoding a light-chain variable region thereof from the hybridoma. Then, the inventors have succeeded in linking the cloned DNA encoding a heavy-chain variable region and the cloned DNA encoding a light-chain variable region to DNA encoding a heavy-chain constant region and DNA encoding a light-chain constant region, respectively, inserting the resultant into a vector, transforming a host cell or a host insect therewith, and producing a recombinant anti-dog IgE antibody, thereby accomplishing the present invention.

Thus, the present invention is as follows.

[1] An anti-dog IgE monoclonal antibody which binds to dog IgE, comprising a heavy-chain variable region consisting of the amino acid sequence represented by SEQ ID NO: 2 and a light-chain variable region consisting of the amino acid sequence represented by SEQ ID NO: 4, or a functional fragment thereof which binds to dog IgE.

[2] An anti-dog IgE monoclonal antibody which binds to dog IgE, comprising a heavy-chain variable region consisting of the amino acid sequence represented by SEQ ID NO: 6 and a light-chain variable region consisting of the amino acid sequence represented by SEQ ID NO: 8, or a functional fragment thereof which binds to dog IgE.

[3] The anti-dog IgE monoclonal antibody which binds to dog IgE or a functional fragment thereof which binds to dog IgE according to [1] or [2], wherein the class of the antibody is IgG, IgA, IgE, or IgM.

[4] The anti-dog IgE monoclonal antibody which binds to dog IgE or a functional fragment thereof which binds to dog IgE according to [3], wherein the subclass of the antibody is IgG1, IgG2, IgG3, or IgG4.

[5] The anti-dog IgE monoclonal antibody which binds to dog IgE or a functional fragment thereof which binds to dog IgE according to any one of [1] to [4], wherein the functional fragment is a peptide fragment selected from the group consisting of Fab, Fab', F(ab')$_2$, disulfide-stabilized Fv (dsFv), dimerized V region (diabody), single chain Fv (scFv), and CDR.

[6] A polypeptide which is a heavy-chain variable region of an anti-dog IgE antibody, consisting of the amino acid sequence represented by SEQ ID NO: 2 or 6.

[7] A polypeptide which is a light-chain variable region of an anti-dog IgE antibody, consisting of the amino acid sequence represented by SEQ ID NO: 4 or 8.

[8] A polynucleotide encoding a heavy-chain variable region of an anti-dog IgE antibody, consisting of the DNA sequence represented by SEQ ID NO: 1 or 5.

[9] A polynucleotide encoding a light-chain variable region of an anti-dog IgE antibody, consisting of the DNA sequence represented by SEQ ID NO: 3 or 7.

[10] A vector comprising the polynucleotide according to [8], the polynucleotide according to [9], or the polynucleotide according to [8], and the polynucleotide according to [9].

[11] A cell comprising the vector according to [10].

[12] A silkworm comprising the vector according to [10].

[13] A method for producing an anti-dog IgE antibody, comprising: linking DNA encoding a heavy-chain variable region of an anti-dog IgE antibody, consisting of the DNA sequence represented by SEQ ID NO: 1 to DNA encoding a heavy-chain constant region of the antibody; linking DNA encoding a light-chain variable region of an anti-dog IgE antibody, consisting of the DNA sequence represented by SEQ ID NO: 3 to DNA encoding a light-chain constant region of the antibody; inserting the resultant DNA constructs into an expression vector, transforming a host cell or a host animal with the vector, and producing an antibody using the host cell or the host animal.

[14] A method for producing an anti-dog IgE antibody, comprising: linking DNA encoding a heavy-chain variable region of an anti-dog IgE antibody, consisting of the DNA sequence represented by SEQ ID NO: 5 to DNA encoding a heavy-chain constant region of the antibody; linking DNA encoding a light-chain variable region of an anti-dog IgE antibody, consisting of the DNA sequence represented by SEQ ID NO: 7 to DNA encoding a light-chain constant region of the antibody; inserting the resultant DNA constructs into an expression vector, transforming a host cell or a host animal with the vector, and producing an antibody using the host cell or the host animal.

[15] The method according to [14], wherein the DNA encoding a heavy-chain constant region of the antibody consists of the DNA sequence represented by SEQ ID NO: 9 and the DNA encoding a light-chain constant region of the antibody consists of the DNA sequence represented by SEQ ID NO: 11.

[16] The method for producing an anti-dog IgE antibody according to [13] or [14], wherein the host animal is a silkworm.

[17] A reagent for detecting a dog allergic disease, comprising the anti-dog IgE monoclonal antibody which binds to dog IgE or a functional fragment thereof which binds to dog IgE according to any one of [1] to [5].

[18] A method for detecting a dog allergic disease, comprising measuring IgE antibody in the blood, serum, or plasma collected from a dog using the anti-dog IgE monoclonal antibody which binds to dog IgE or a functional fragment thereof which binds to dog IgE according to any one of [1] to [5].

[19] A reagent for detecting a dog allergic disease, comprising the polypeptide according to [6] or [7].

[20] A method for detecting a dog allergic disease, comprising measuring IgE antibody in the blood, serum, or plasma collected from a dog using the polypeptide according to [6] or [7].

The present specification encompasses the contents of the specification and/or drawings of Japanese Patent Application No. 2013-057015 on which the priority of the present application is based.

Advantageous Effects of Invention

The monoclonal antibody comprising a heavy-chain variable region and a light-chain variable region of an anti-dog IgE antibody according to the present invention can bind with high affinity to dog IgE and can be suitably used, for example, for treating a dog allergic disease. The polynucleotide encoding the heavy-chain variable region and the polynucleotide encoding light-chain variable region according to the present invention can be used to efficiently and repeatedly prepare an anti-dog IgE monoclonal antibody.

BRIEF DESCRIPTION OF DRAWINGS

FIG. 17-1 is a graph showing the results of the reactivity test of an anti-dog IgE recombinant antibody purified from a silkworm body fluid by an ELISA method, and shows the results of examining the silkworm body fluid, the HisTag eluate, and the ion-exchanged antibody (dilution 5-fold to 50-fold).

FIG. 17-2 is a graph showing the results of the reactivity test of an anti-dog IgE recombinant antibody purified from a silkworm body fluid by an ELISA method, and shows the results of examining a ion-exchanged purified product by further proceeding with the dilution (20- to 1,000-fold dilution).

FIG. 19 is a list showing the sequences of primers.

DESCRIPTION OF EMBODIMENTS

Figure 1:
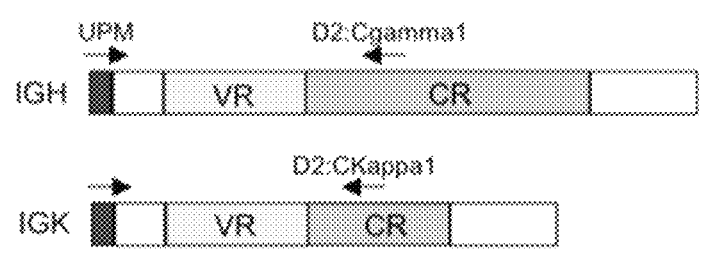
FIG. 1 is a diagram showing the schematic of cloning of the heavy-chain and light-chain variable regions of monoclonal antibodies (mouse-derived H5 and rat-derived X1).

The present invention will be described below in detail.

The present invention is a heavy-chain variable region or a light-chain variable region of an anti-dog IgE antibody which specifically binds to animal IgE, and polynucleotides encoding the variable regions. In addition, the present invention is an anti-dog IgE monoclonal antibody comprising the heavy-chain variable region and the light-chain variable region, which specifically binds to animal IgE. The anti-dog IgE antibody of the present invention can recognize and bind to dog IgE and the IgE of other mammals such as mice. The antibody of the present invention encompasses a functional fragment of the antibody or a modified product thereof. For example, the functional fragment of the antibody is a fragment of the antibody, which specifically binds to the antigen. Examples of the functional fragment include Fab, F(ab')2, Fv, Fab/c having one Fab and complete Fc, and single-chain Fv (scFv) in which an H chain or an L chain is linked through a suitable linker. The polynucleotide encompasses DNA and RNA.

The nucleotide sequence of DNA encoding the heavy-chain variable region of the anti-dog IgE antibody of the present invention consists of the sequence represented by SEQ ID NO: 1 or 5, and the amino acid sequence of the heavy-chain variable region consists of the sequence represented by SEQ ID NO: 2 or 6. The amino acid sequence represented by SEQ ID NO: 2 is encoded by the nucleotide sequence represented by SEQ ID NO: 1, and the amino acid sequence represented by SEQ ID NO: 6 is encoded by the nucleotide sequence represented by SEQ ID NO: 5. The heavy-chain variable regions represented by SEQ ID NOS: 1 and 2 are derived from a mouse anti-dog IgE monoclonal antibody, and the heavy-chain variable regions represented by SEQ ID NOS: 5 and 6 are derived from a rat anti-dog IgE monoclonal antibody. The nucleotide sequence of DNA encoding the light-chain variable region of the anti-dog IgE antibody of the present invention consists of the sequence represented by SEQ ID NO: 3 or 7, and the amino acid sequence of the light-chain variable region consists of the sequence represented by SEQ ID NO: 4 or 8. The amino acid sequence represented by SEQ ID NO: 4 is encoded by the nucleotide sequence represented by SEQ ID NO: 3, and the amino acid sequence represented by SEQ ID NO: 8 is encoded by the nucleotide sequence represented by SEQ ID NO: 7. The light-chain variable regions represented by SEQ ID NOS: 3 and 4 are derived from a mouse anti-dog IgE monoclonal antibody, and the light-chain variable regions represented by SEQ ID NOS: 7 and 8 are derived from a rat anti-dog IgE monoclonal antibody. In other words, the heavy-chain variable region of the present invention is a polypeptide consisting of the amino acid sequence represented by SEQ ID NO: 2 or 6, and the light-chain variable region of the present invention is a polypeptide consisting of the amino acid sequence represented by SEQ ID NO: 4 or 8.

The anti-dog IgE antibody of the present invention is an antibody comprising the above heavy-chain variable region or an antibody comprising the above light-chain variable region. Preferably, it is an antibody comprising both of the heavy-chain variable region and the light-chain variable region or a functional fragment thereof. The anti-dog IgE antibody of the present invention is, for example, an antibody comprising a heavy-chain variable region consisting of the amino acid sequence represented by SEQ ID NO: 2 and a light-chain variable region consisting of the amino acid sequence represented by SEQ ID NO: 4, or an antibody comprising a heavy-chain variable region consisting of the amino acid sequence represented by SEQ ID NO: 6 and a light-chain variable region consisting of the amino acid sequence represented by SEQ ID NO: 8.

The heavy-chain variable region and the light-chain variable region according to the present invention are polypeptides contained in the antigen recognition site of an antibody recognizing and binding to dog IgE or a fragment of the antibody.

The heavy-chain variable region or the light-chain variable region of the anti-dog IgE antibody which specifically binds to animal IgE according to the present invention can be obtained by using dog IgE as an immunogen, acquiring an anti-IgE antibody-producing hybridoma by a well-known method using mouse or rat cells, isolating DNA encoding a heavy-chain variable region or DNA encoding a light-chain variable region from the hybridoma, and expressing the DNA.

The anti-dog IgE monoclonal antibody which specifically binds to animal IgE, comprising the heavy-chain variable region and the light-chain variable region is composed of the heavy-chain variable region and the heavy-chain constant region and the light-chain variable region and the light-chain constant region. The heavy-chain constant region is composed of 3 domains, i.e., $C_H1$, $C_H2$, and $C_H3$. The heavy-chain constant region may be the constant region of IgG1, IgG2, IgG3, IgG4, IgA, IgM, or IgD; however, the most preferred is the constant region of IgG1 or IgG4. The light-chain constant region is composed of one domain, i.e., $C_L$. The light-chain constant region is a κ or λ constant region.

The DNA encoding an antibody can be obtained as DNA encoding a heavy chain and DNA encoding a light chain by linking DNA encoding a heavy-chain variable region to DNA encoding a heavy-chain constant region and further linking DNA encoding a light-chain variable region to DNA encoding a light-chain constant region. The organism species from which the variable region is derived may be different from the animal species from which the constant region is derived; the anti-dog IgE antibody of the present invention includes a chimeric antibody in which the organism species from which the variable region is derived is different from the organism species from which the constant region is derived. For example, although the heavy-chain variable region encoded by the DNA represented by SEQ ID NO: 1 and the light-chain variable region encoded by the DNA represented by SEQ ID NO: 3 are mouse-derived, these DNAs can be linked to DNAs encoding the constant regions of a rat-derived antibody to prepare a chimeric antibody containing the mouse-derived variable regions and the rat-derived constant regions. Examples of the constant region of the rat-derived antibody include the heavy-chain constant region of IgG2b antibody, consisting of the amino acid sequence represented by SEQ ID NO: 10 and the light-chain constant region of an Ig κ chain, consisting of the amino acid sequence represented by SEQ ID NO: 12. The DNA nucleotide sequence encoding the amino acid sequence represented by SEQ ID NO: 10 is represented by SEQ ID NO: 9, and the DNA nucleotide sequence encoding the amino acid sequence represented by SEQ ID NO: 12 is represented by SEQ ID NO: 11.

The anti-dog IgE antibody further encompasses a chimeric antibody having the constant region of a human antibody.

The antibody of the present invention is, for example, a heterotetrameric protein which comprises a heavy chain in which the heavy-chain variable region consisting of the amino acid sequence represented by SEQ ID NO: 2 is linked to the heavy-chain constant region consisting of the amino acid sequence represented by SEQ ID NO: 10 and a light chain in which the light-chain variable region consisting of the amino acid sequence represented by SEQ ID NO: 4 is linked to the light-chain constant region consisting of the amino acid sequence represented by SEQ ID NO: 12, and is composed of 2 heavy chains and 2 light chains. The antibody of the present invention is also, for example, a heterotetrameric protein which comprises a heavy chain in which the heavy-chain variable region consisting of the amino acid sequence represented by SEQ ID NO: 6 is linked to the heavy-chain constant region consisting of the amino acid sequence represented by SEQ ID NO: 10 and a light chain in which the light-chain variable region consisting of the amino acid sequence represented by SEQ ID NO: 8 is linked to the light-chain constant region consisting of the amino acid sequence represented by SEQ ID NO: 12, and is composed of 2 heavy chains and 2 light chains. The nucleotide sequence of the heavy-chain variable region of mouse H5 monoclonal antibody linked to the rat IgG2b constant region is shown in SEQ ID NO: 13, and the nucleotide sequence of the heavy-chain variable region of a rat X1 monoclonal antibody linked to the rat IgG2b constant region is shown in SEQ ID NO: 15. The nucleotide sequence of the light-chain variable region of the mouse H5 monoclonal antibody linked to the rat Ig κ constant region is shown in SEQ ID NO: 14, and the nucleotide sequence of the light-chain variable region of the rat X1 monoclonal antibody linked to the rat Ig κ constant region is shown in SEQ ID NO: 16. The sequences represented by SEQ ID NOS: 13 to 16 each comprise a sequence encoding a His-tag consisting of 6 histidine (His) residues 3' thereto.

The heavy-chain variable region includes not only the heavy-chain variable region consisting of the amino acid sequence represented by SEQ ID NO: 2 or 6 but also a heavy-chain variable region consisting of a protein having the activity of the heavy-chain variable region of the antibody, consisting of an amino acid sequence in which 1 or several, e.g., 1 to 10, preferably 1 to 5, more preferably 1 or 2, still more preferably 1, amino acids are deleted, substituted, or added in the amino acid sequence. The light-chain variable region includes not only the light-chain variable region consisting of the amino acid sequence represented by SEQ ID NO: 4 or 8 but also a light-chain variable region consisting of a protein having the activity of the light-chain variable region of the antibody, consisting of an amino acid sequence in which 1 or several, e.g., 1 to 10, preferably 1 to 5, more preferably 1 or 2, still more preferably 1, amino acids are deleted, substituted, or added in the amino acid sequence. The heavy-chain constant region includes not only the heavy-chain variable region consisting of the amino acid sequence represented by SEQ ID NO: 10 but also a heavy-chain constant region consisting of a protein having the activity of the heavy-chain constant region of the antibody, consisting of an amino acid sequence in which 1 or several, e.g., 1 to 10, preferably 1 to 5, more preferably 1 or 2, still more preferably 1, amino acids are deleted, substituted, or added in the amino acid sequence. The light-chain constant region includes not only the light-chain variable region consisting of the amino acid sequence represented by SEQ ID NO: 12 but also a light-chain constant region consisting of a protein having the activity of the light-chain constant region of the antibody, consisting of an amino acid sequence in which 1 or several, e.g., 1 to 10, preferably 1 to 5, more preferably 1 or 2, still more preferably 1, amino acids are deleted, substituted, or added in the amino acid sequence.

Examples of the amino acid sequence in which 1 or several amino acids are deleted, substituted, or added in the amino acid sequence of SEQ ID NO: 2, 6, 4, 8, 10, or 12 include an amino acid sequence having at least 85% or more sequence identity with the amino acid sequence of SEQ ID NO: 2, 6, 4, 8, 10, or 12, preferably 90% or more, more preferably 95% or more, particularly preferably 97% or more, when calculated, for example, using BLAST (Basic Local Alignment Search Tool at the National Center for Biological Information) (e.g., default, or initial parameters).

The protein having an amino acid sequence in which 1 or several amino acids are deleted, substituted, or added in the amino acid sequence of SEQ ID NO: 2, 6, 4, 8, 10, or 12 is substantially identical to the protein having the amino acid sequence of SEQ ID NO: 2, 6, 4, 8, 10, or 12.

The DNA encoding the heavy-chain variable region, the light-chain variable region, the heavy-chain constant region, or the light-chain constant region of the antibody of the present invention also includes DNA encoding a protein having the activity of the heavy-chain variable region, the light-chain variable region, the heavy-chain constant region, or the light-chain constant region of the antibody, having at least 85% or more sequence identity with the nucleotide sequence consisting of the sequence represented by SEQ ID NO: 1, 3, 5, 7, 9, or 11, preferably 90% or more, more preferably 95% or more, particularly preferably 97% or more, when calculated, for example, using BLAST (Basic Local Alignment Search Tool at the National Center for Biological Information) (e.g., default, or initial parameter).

The DNA encoding the heavy-chain variable region, the light-chain variable region, the heavy-chain constant region, or the light-chain constant region of the antibody according to the present invention also includes DNA encoding a protein having the activity of the heavy-chain variable region, the light-chain variable region, the heavy-chain constant region, or the light-chain constant region of the antibody, capable of being hybridized to DNA consisting of a sequence complementary to DNA consisting of the sequence represented by SEQ ID NO: 1, 3, 5, 7, 9, or 11 under the following stringent conditions. Specifically, the conditions refer to conditions enabling identification by performing hybridization at 68° C. in the presence of 0.7 to 1.0 M NaCl using a DNA-immobilized filter, followed by washing at 68° C. using an SSC solution with a 0.1 to 2 times higher concentration (an SSC solution with a 1 time concentration consists of 150 mM NaCl and 15 mM sodium citrate). Alternatively, the DNA is DNA capable of forming a hybrid by transferring the DNA to a nitrocellulose membrane by a Southern blotting method for immobilization, followed by reaction at 42° C. overnight in a hybridization buffer solution [50% formamide, 4×SSC, 50 mM HEPES (pH 7.0), 10×Denhardt's solution, 100 µg/ml salmon sperm DNA]

The heavy-chain variable region or the light-chain variable region of the present invention can be produced in cells by inserting DNA encoding the heavy-chain variable region or DNA encoding the light-chain variable region into an expression vector, transforming a host cell for expression with the vector, and culturing the host cell.

The anti-dog IgE monoclonal antibody of the present invention can be produced by inserting DNA encoding the heavy chain and DNA encoding the light chain into an expression vector, transforming a host cell with the vector, and culturing the host cell. Here, the DNA encoding the heavy chain and the DNA encoding the light chain may be inserted into the same vector, followed by transforming a host cell with the vector, or the DNA encoding the heavy chain and the DNA encoding the light chain may be inserted into separate vectors, followed by transforming a host cell with the 2 vectors. Here, the DNAs encoding the heavy-chain variable region and the light-chain variable region may be inserted into a vector into which DNAs encoding the heavy-chain constant region and the light-chain constant region of a particular isotype are inserted in advance. The vector may contain DNA encoding a signal peptide for promoting the secretion of an antibody from a host cell, where the DNA encoding the signal peptide is linked in-frame to the DNA encoding the antibody. After the production of the antibody, the signal peptide can be removed to provide the antibody as a mature protein.

Here, the DNA encoding the heavy-chain variable region, the DNA encoding the light-chain variable region, the DNA in which the DNA encoding the heavy-chain variable region is linked to the DNA encoding the heavy-chain constant region, or the DNA in which the DNA encoding the light-chain variable region is linked to the DNA encoding the light-chain constant region may be functionally linked to elements such as a promotor, an enhancer, and a polyadenylation signal. "Functionally linked" as used here refers to that these elements are linked thereto so that they can fulfill their functions.

The promotor and the enhancer used may be a promotor and an enhancer derived from cytomegalovirus (CMV), simian virus 40 (SV40), or adenovirus.

The vector for inserting a gene according to the present invention is not particularly limited provided that it can be replicated in a host, such as bacteria, yeast, or animal cells; examples thereof include plasmids and phages. The vector used for constructing the expression vector may be a well-known one. Examples thereof include Flexi (R) vector (Promega Corporation), pUC19, pTV118 N (Takara Shuzo Co., Ltd.), pUEX2 (Amersham plc), pGEX-4T, pKK233-2 (Pharmacia Corporation), and pMAM-neo (Clontech Laboratories, Inc.). When the variable region or the antibody is produced using a silkworm, pBM030, pBM034, or the like as a silkworm cloning vector may be used.

The expression vector can be introduced into a host cell by a well-known method to transform the host cell. Examples of the method include an electroporation method, a calcium phosphate precipitation method, and a DEAE-dextran transfection method.

The host cell may be prokaryotic cells, such as *Escherichia coli* or *Bacillus subtilis*, as well as eukaryotic cells, such as yeast or animal cells; however, eukaryotic cells are preferably used. Examples of the yeast include *Saccharomyces cerevisiae*, and examples of the animal cells include 293 cells as a human fetal kidney cell line, Chinese hamster ovary (CHO) cells, Sf 21 cells, Sf 9 cells, and TN5 cells as cells of a lepidopteran insect, such as silkworm, simian COS cells, and mouse fibroblasts. The variable region or the antibody of the present invention can also be produced using a silkworm body. The production using a silkworm body can be carried out by a well-known method.

The expressed or produced antibody may be purified using separation and purification methods used for common proteins. For example, the antibody can be separated and purified by properly selecting and combining chromatography, such as affinity chromatography, filter, ultrafiltration, salting-out, and dialysis (Antibodies A Laboratory Manual. Ed Harlow, David Lane, Cold Spring Harbor Laboratory, 1988). The anti-dog IgE antibody can also be produced in an affinity-tagged state and then purified by affinity chromatography using the affinity tag. Examples of the affinity tag sequence include a polyhistidine sequence consisting of 2 to 12, preferably 4 or more, more preferably 4 to 7, still more preferably 5 or 6 histidine residues. Here, the synthetic protein can be purified using nickel chelate column chromatography using nickel as a ligand. It can also be purified by affinity chromatography using a column on which an antibody to the polyhistidine is immobilized as a ligand. In addition, HAT-tag, HN-tag, or the like consisting of a histidine-containing sequence can also be used. Further, other affinity tags include, for example, V5-tag, Xpress-tag, AU1-tag, T7-tag, VSV-G-tag, DDDDK-tag, S-tag, Cruz-Tag09, CruzTag22, CruzTag41, Glu-Glu-tag, Ha.11-tag, and KT3-tag. The present invention encompasses anti-dog IgE antibodies to which these tags bind.

The anti-dog IgE antibody which specifically binds to animal IgE and a functional fragment thereof which binds to dog IgE according to the present invention recognize and bind to dog IgE. The antibody comprising the heavy-chain variable region consisting of the amino acid sequence represented by SEQ ID NO: 6 and the light-chain variable region consisting of the amino acid sequence represented by SEQ ID NO: 8 and a functional fragment thereof which binds to dog IgE recognize and bind to dog IgE and mouse IgE.

The anti-dog IgE antibody or a functional fragment thereof which binds to dog IgE according to the present invention can be used as an agent for treating an allergic disease in dogs and other animals. The allergic disease is an IgE-mediated type I allergic disease, and examples of the IgE-mediated allergic disease include atopic dermatitis, pollinosis, food allergy, allergic rhinitis, asthma, allergic conjunctivitis, mite allergic disease, urticaria, anaphylactic shock, and PIE (pulmonary infiltration with eosinophilia) syndrome. The anti-IgE antibody which specifically binds to animal IgE can prevent or treat an IgE-mediated allergic disease in the animal by preventing IgE from binding to mast cells or basophils.

The anti-dog IgE antibody or a functional fragment thereof which binds to dog IgE according to the present invention can also be used as a DNA vaccine for preventing or treating an allergic disease.

The prevention or treatment agent of the present invention may be in the form of sterile, aqueous or nonaqueous solutions, suspensions, or emulsions. In addition, the agent may contain a pharmaceutically acceptable diluent, such as salt, buffer, or adjuvant, an auxiliary agent, a carrier, and the like. The prevention or treatment agent can be administered through routes, such as oral, nasal, transmucosal, intramuscular or subcutaneous, intranasal, intratracheal, dermal, transdermal, and intradermal routes.

The dose of the prevention or treatment agent of the present invention can vary depending on the animal species receiving administration; however, the dose is a few tens of ng to a few mg per administration. The agent may be administered in single dose, or may be administered on several occasions at 2-day to 8-week intervals.

In addition, the anti-dog IgE antibody of the present invention can be used for detecting an allergic disease in dogs and the like. The present invention encompasses a detection reagent for detecting an allergic disease, comprising the anti-dog IgE antibody of the present invention, or the heavy-chain variable region or the light-chain variable region thereof. For example, an allergic disease can be detected by collecting a blood, serum, or plasma sample from a dog and detecting IgE antibody in the sample.

The antibody comprising the heavy-chain variable region consisting of the amino acid sequence represented by SEQ ID NO: 6 derived from rat X1 antibody and the light-chain variable region consisting of the amino acid sequence represented by SEQ ID NO: 8 binds to not only dog IgE but also mouse IgE. Thus, in taking preclinical data on a treatment agent for dogs, the immune reaction in dogs can be known by examining the immune reaction in mice using the antibody, enabling the development of a treatment agent for dogs without using dogs as test subjects.

EXAMPLES

The present invention is described below in detail, based on Examples. However, the present invention is not intended to be limited by these Examples.

Example 1

Preparation of Recombinant-Type Anti-Dog IgE Antibody (H5 (CCH3-5), X1)

1. Cloning of Heavy-Chain/Light-Chain Variable Region of Monoclonal Antibody (Mouse-Derived H5 and Rat-Derived X1)
   1) Total RNAs were extracted from hybridoma cells secreting H5 (CCH3-5) and X1 monoclonal antibodies as anti-dog IgE monoclonal antibodies (H5 cell RNA: 115 ng/μL, X1 cell RNA: 225 ng/μL).

2) 5'-RACE-Ready cDNAs were synthesized using SMARTer™ RACE cDNA Amplification Kit (Cat. No. 634293) from Clontech Laboratories, Inc. As templates, H5 monoclonal antibody-producing hybridoma RNA and X1 monoclonal antibody-producing hybridoma RNA were used in amounts of 316 ng and 618 ng, respectively; reaction was carried out as prescribed in the manual. After synthesis, the resultants were each diluted by adding 100 μL of TE, and preserved at −30° C.

3) It is known that the H5 monoclonal antibody is an antibody molecule consisting of a combination of mouse IgG1 and κ with the X1 monoclonal antibody being an antibody molecule consisting of a combination of rat IgG2b and κ; thus, a reverse primer specific for each constant region (hereinafter, abbreviated as CR) was designed. Using this and Universal Primer (contained in the kit, hereinafter abbreviated as UPM) for a consensus sequence present at the 5' terminal of 5'-RACE-Ready cDNA, PCR reaction was carried out to increase the variable region (hereinafter, abbreviated as VR).

FIG. 1 shows the schematic of a method for cloning the heavy-chain and light-chain variable regions of monoclonal antibodies (mouse-derived H5 and rat-derived X1).

The following primers were used.

UPM
Long
(SEQ ID NO: 17)
5'-CTAATACGACTCACTATAGGGCAAGCAGTGGTATCAACGCAGAGT-3'

Short
(SEQ ID NO: 18)
5'-CTAATACGACTCACTATAGGGC-3'

D2: Cgamma1 (common to IgG1 and 2b in mice and rats)

(SEQ ID NO: 19)
5'-AGGGAAATARCCCTTGACCAG-3'

D2: CkapPa1 (IGKC1 and 2 in mice and rats contains only an internal 1-2 nucleotide mismatch)

(SEQ ID NO: 20)
5'-GCACCTCCAGATGTTAACTG-3'

4) Expected sizes of PCR products were electrophoretically obtained for both of the H5 monoclonal antibody and the X1 monoclonal antibody; thus, each cDNA fragment was excised and purified using Wizard SV Gel and PCR Clean-up System (#A9282) from Promega Corporation.

5) The purified fragments were each cloned into pTA2 vector using Target Clone™-Plus-(No. TAK-201) from Toyobo Co., Ltd.

6) The fragments cloned in 5) were each subjected to sequence analysis, and the resultant sequence was searched using IMGT/V-QUEST (www.imgt.org/IMGT_vquest) from IMGT (Immuno Gene Tics). The results are shown in Table 1. H5_HVR denotes the heavy-chain variable region of mouse-derived H5 monoclonal antibody; H5_KVR, the light-chain (κ chain) variable region of mouse-derived H5 monoclonal antibody; X1_HVR, the heavy-chain variable region of rat-derived X1 monoclonal antibody; and X1_KVR, the light-chain (κ chain) variable region of rat-derived X1 monoclonal antibody. The nucleotide sequence for the heavy-chain variable region of mouse-derived H5 monoclonal antibody is shown in SEQ ID NO: 1, and the amino acid sequence thereof is shown in SEQ ID NO: 2. The nucleotide sequence for the light-chain (κ chain) variable region of mouse-derived H5 monoclonal antibody is shown in SEQ ID NO: 3, and the amino acid sequence thereof is shown in SEQ ID NO: 4. The nucleotide sequence for the heavy-chain variable region of rat-derived X1monoclonal antibody is shown in SEQ ID NO: 5, and the amino acid sequence thereof is shown in SEQ ID NO: 6. In addition, the nucleotide sequence for the light-chain (κ chain) variable region of rat-derived X1 monoclonal antibody is shown in SEQ ID NO: 7, and the amino acid sequence thereof is shown in SEQ ID NO: 8.

TABLE 1

| Species | Clone | Functionality (Functionality) | V-GENE and Allele |
|---|---|---|---|
| Mouse | IGH_H5(H5_HVR) | Productive | Musmus IGHV1S135*01 |
| Mouse | IGK_H5(H5_KVR) | Productive | Musmus IGKV1-110*01 |
| Rat | IGH_X1(X1_HVR) | Productive | IGHV8S11*01 |
| Rat | IGK_X1(X1_KVR) | Productive | IGKV1S14*01 |

2. Linkage of Each of Heavy-Chain H5_VR (Variable Region) and Heavy-Chain X1_VR (Variable Region) to Rat IgG2b Constant Region (Hereinafter, Abbreviated as CR)

Figure 2:
FIG. 2 is a series of diagrams showing the schematic of linkage of heavy chain H5_VR and heavy chain X1_VR to the rat IgG2b constant region.
Figure 2:
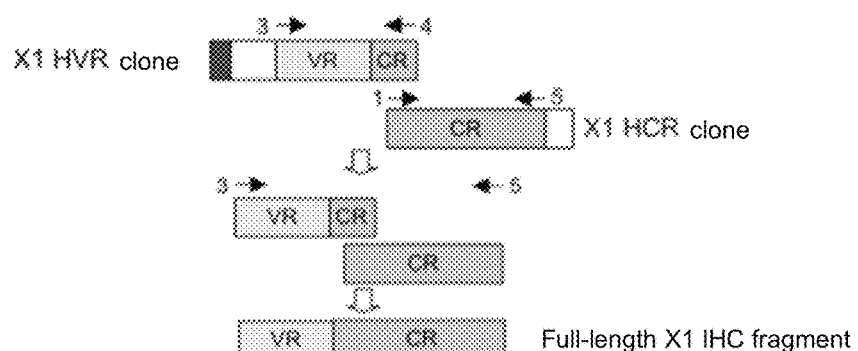
Figure 2:
Figure 2:
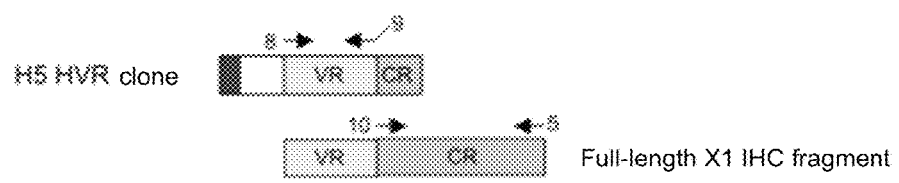
Figure 2:
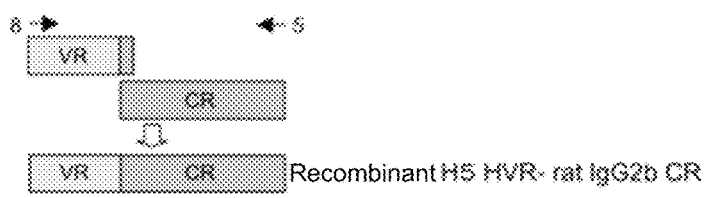
Figure 2:

FIG. 2 shows the schematic of a method for linking each of heavy-chain H5_VR and heavy-chain X1_VR to the rat IgG2b constant region.

1) Using the above-described 5'-RACE-Ready cDNA synthesized from X1 monoclonal antibody RNA as a template, CR of the X1 heavy chain was amplified such that the CR overlapped with the CR portion contained in VR region cloning. Primers were designed with reference to the rat CR sequence, which is known (The sequence of the primers is shown in FIG. 19. The amplified cDNA fragment was purified as described above, cloned in pTA2 vector, and then subjected to sequence analysis to confirm that the sequence is the known rat IgG 2b sequence (X1 HCR clone) (FIG. 2A).

2) cDNA fragments were amplified from an X1 VR clone and an X1 CR clone using primers 3 and 4 and primers 1 and 5, respectively, followed by purification; a mixture thereof was further subjected to PCR reaction using primers 3 and 5 as templates to provide a full-length rat X1 IHC fragment (FIG. 2B).

3) For cloning into an expression vector and expression confirmation analysis, a fragment obtained by adding the SgfI site 5' to the IHC fragment and His Tag 3' thereto was amplified using primers 6 and 7 (FIG. 2C).

4) From a H5 VR clone, a H5 HVR cDNA fragment in which a rat CR sequence is added to the VR region using primers 8 and 9 was obtained. A rat IgG2b CR fragment was also obtained from the full-length X1 IHC fragment obtained in 2) using primers 10 and 5 (FIG. 2D).

5) A mixture of the mouse H5 HVR cDNA fragment and the rat IgG2b CR cDNA fragment obtained in 4) was used as a template to subject a recombinant IHC fragment of mouse H5 HVR-rat IgG2b CR to PCR amplification using primers 8 and 5 (FIG. 2E).

6) A fragment obtained by adding the SgfI site 5' to the fragment and His Tag 3' thereto was amplified using primers 11 and 7 as in 3) (FIG. 2F).

7) As a vector into which the fragment is to be incorporated, pF4A CMV Flexi Vector (Promega Corporation, #C8481) was digested with SgfI/PmeI and purified (the resultant vector enables the insertion of the PCR fragment into the SgfI/blunt end, and TOYOBO KOD Plus-ver. 2 (#KOD-211, no addition of -A) was used for a series of PCR reactions, enabling the insertion into the SgfI/blunt end).

8) The cDNA fragments obtained in 3) and 6) were each digested with sgfI enzyme, ligated to the vector provided in 7), and transformed into One Shot Max Efficiency DH10B T1 Phage Resistant Competent Cell (Life Technologys, #12331-013).

9) A clone positive in colony PCR was screened, and after plasmid purification, sequence confirmation was carried out by sequence analysis. The nucleotide sequence for the heavy-chain variable region of the mouse H5 monoclonal antibody linked to the rat IgG2b constant region is shown in SEQ ID NO: 13, and the nucleotide sequence for the heavy-chain variable region of the rat X1 monoclonal antibody linked to the rat IgG2b constant region is shown in SEQ ID NO: 15. The nucleotide sequence for the rat IgG2b constant region is shown in SEQ ID NO: 9, and the amino acid sequence thereof is shown in SEQ ID NO: 10.

3. Linkage of Each of Light-Chain H5_VR (Variable Region) and Light-Chain X1_VR (Variable Region) to Rat Ig κ Constant Region (CR)

Figure 3:
FIG. 3 is a series of diagrams showing the schematic of linkage of light chain H5_VR and light chain X1_VR to the rat Ig κ constant region (CR).
Figure 3:
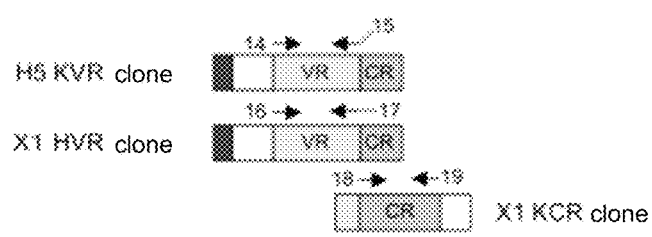
Figure 3:
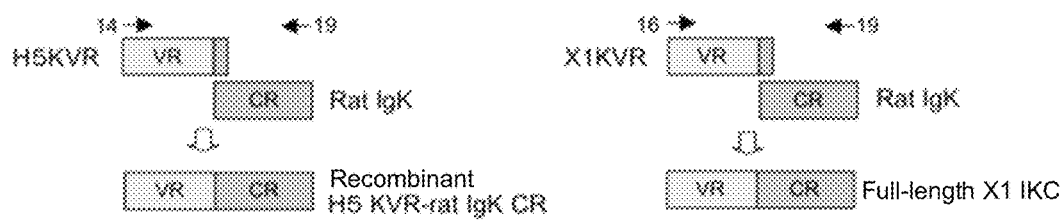
Figure 3:
Figure 3:

FIG. 3 shows the schematic of a method for linking each of Light-chain H5_VR and Light-chain X1_VR to the rat Ig κ constant region (CR).

1) The 5'-RACE-Ready cDNA synthesized from X1 RNA was used as a template like the heavy-chain to subject the X1 light-chain CR cDNA fragment to PCR amplification using primers 12 and 13, and the cDNA fragment was purified, cloned into pTA2 vector, and subjected to sequence analysis as in 2. above to confirm that the sequence is the known rat Ig κ sequence (X1 KCR clone) (FIG. 3A).

2) From H5 KVR clone and X1 KVR clone, H5 KVR cDNA and 1 KVR cDNA fragments in each of which the rat KCR sequence was added to the VR region were obtained using primers 14 and 15 and primers 16 and 17, respectively. From the X1 KCR clone obtained in 1), a rat IgK CR fragment was obtained using primers 18 and 19 (FIG. 3B).

3) The H5 KVR cDNA and X1 KVR cDNA fragments obtained in 2) were each mixed with a rat IgK CR cDNA fragment, and these mixtures were used as templates to perform PCR reaction using primers 14 and 19 and primers 16 and 19 to amplify a recombinant IKC of mouse H5 KVR-rat IgK CR and a full-length rat X1 IKC (FIG. 3C).

4) Like the heavy chain, the sgf I site and His Tag were added 5' and 3', respectively to mouse H5 recombinant IKC and a full-length rat X1 IKC using primers 20 and 21 and primers 22 and 21 (FIG. 3D).

5) Hereinafter, like the heavy chain, SgfI digestion, ligation, transformation, and sequence analysis were carried out to provide the clones. The nucleotide sequence for the light-chain variable region of the mouse H5 monoclonal antibody linked to the rat Ig κ constant region is shown in SEQ ID NO: 14, and the nucleotide sequence for the light-chain variable region of the rat X1 monoclonal antibody linked to the rat Ig κ constant region is shown in SEQ ID NO: 16. The nucleotide sequence for the rat Ig κ constant region is shown in SEQ ID NO: 11, and the amino acid sequence thereof is shown in SEQ ID NO: 12.

4. Expression and Analysis in FreeStyle 293F Cell

1) Plasmids for the mouse H5_HVR-rat IgG2b_CR, the mouse H5_KVR-rat IgKCR, the rat X1_IHC, and the rat X1_IKC were each purified and adjusted to 1 μg/μL.

2) Using FreeStyle 293 Expression System (Life Technologies), the recombinant H5 monoclonal antibody and X1 monoclonal antibody were each expressed and secreted in 3 mL of the culture system, and 2 days after transfection, the culture supernatant was recovered. The samples used are shown in Table 2. In Table 2, H5_ratCR as a sample name indicates the variable region of the mouse H5 monoclonal antibody linked to the constant region of the rat antibody; H5_HC as a plasmid name indicates the heavy-chain variable region of the mouse H5 monoclonal antibody linked to the rat IgG2b constant region; and H5_KC indicates the light-chain variable region of the mouse H5 monoclonal antibody linked to the rat Ig κ constant region. X1_ratCR as a sample name indicates the variable region of the rat X1 monoclonal antibody linked to the constant region of the rat antibody, and X1_HC as a plasmid name indicates the heavy-chain variable region of the rat X1 monoclonal antibody linked to the rat IgG2b constant region, and X1_KC indicates the light-chain variable region of the rat X1 monoclonal antibody linked to the rat Ig κ constant region. The antibody represented by H5_ratCR is an antibody having the variable region of the mouse H5 monoclonal antibody and the constant region of the rat antibody, and the antibody represented by X1_ratCR is an antibody having the variable region of the rat X1 monoclonal antibody and the constant region of the rat antibody.

TABLE 2

| Sample Name | Plasmid Name | Vector | Tag | Transfection (1 μg/μL Plasmid) |
|---|---|---|---|---|
| H5_ratCR | H5_HC | pF4A | His | 1.6 μL |
|  | H5_KC | pF4A | His | 1.4 μL |
| X1_ratCR | X1_HC | pF4A | His | 1.6 μL |
|  | X1_KC | pF4A | His | 1.4 μL |

3) The secreted antibody was subjected to characterization. The characterization was performed for concentration prediction by Western blot analysis using an anti-HisTag antibody and dot-blotting using the anti-HisTag antibody and on reactivity to dog, mouse and human IgE proteins using dot-blotting.

Figure 4:
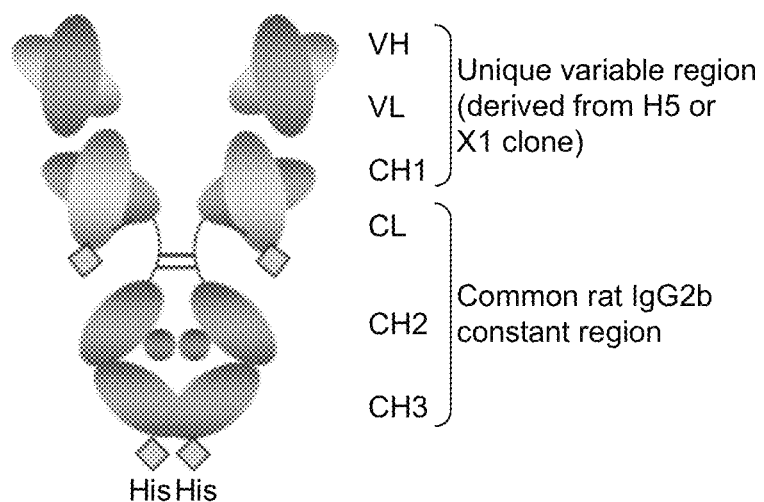
FIG. 4 is a diagram showing a structure of an antibody produced using FreeStyle 293F cells.

The structure of the produced antibody is shown in FIG. 4 (the circle indicates sugar modification).

Figure 5:
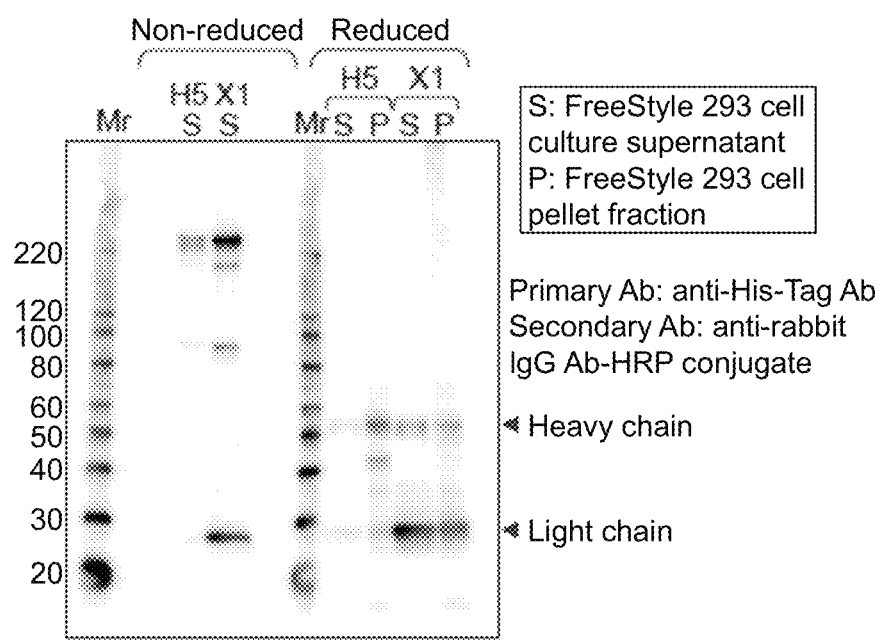
FIG. 5 is a photograph showing the results of Western blot analysis of antibody production using an anti-HisTag antibody for the antibody produced using FreeStyle 293F cells.
Figure 6:
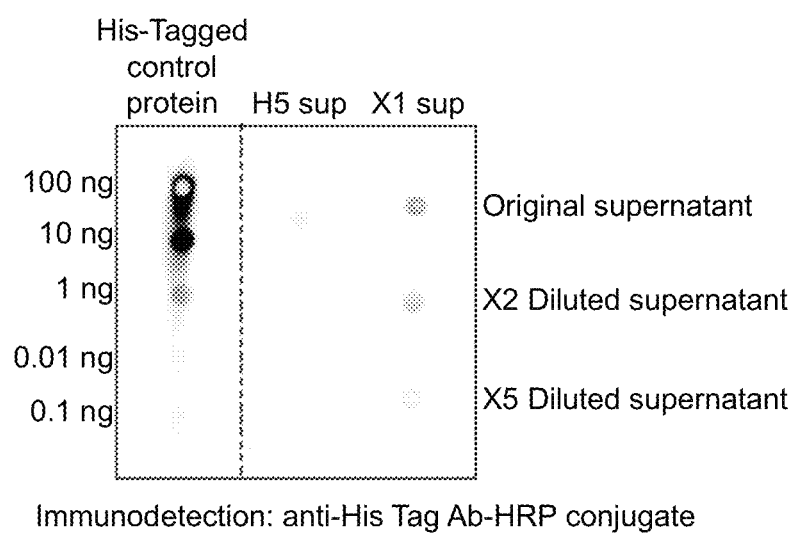
FIG. 6 is a photograph showing the results of concentration (expression level) prediction by dot blot using an anti-HisTag antibody for the antibody produced using FreeStyle 293F cells.
Figure 7:
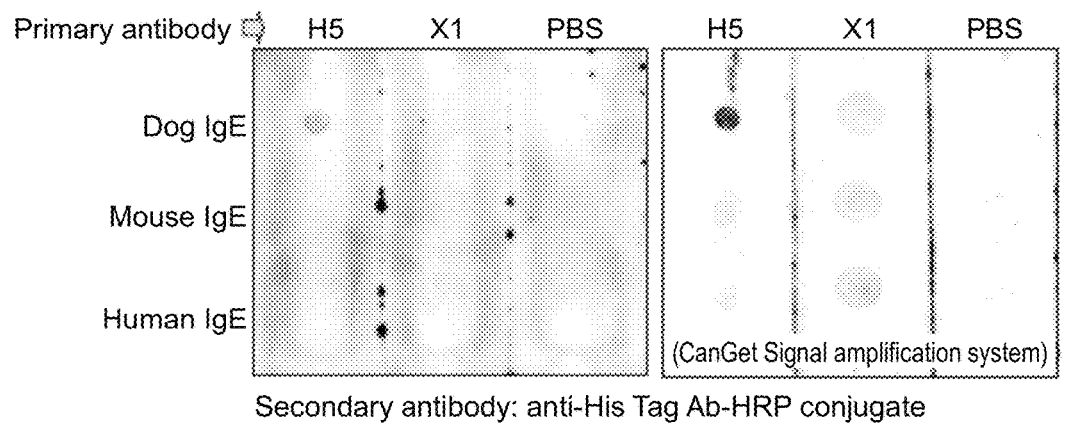
FIG. 7 is a photograph showing the results of confirmation of the reactivity of a produced antibody to dog, mouse, and human IgE proteins by dot blot for the antibody produced using FreeStyle 293F cells.

The results of Western blot analysis of antibody production using an anti-HisTag antibody are shown in FIG. 5. The results of concentration (expression level) prediction by dot-blotting using an anti-HisTag antibody are shown in FIG. 6. The results of confirmation of reactivity of the produced antibody to dog, mouse and human IgE proteins using dot-blotting are shown in FIG. 7. The left panel in FIG. 7 shows the results of amplifying the signal. The amount of the antibody produced was lower for the antibody having the variable region of H5 than for the antibody having the variable region of X1, and 0.04 μg/mL for the antibody having the variable region of H5 and 0.2 μg/mL for the antibody having the variable region of X1 when converted using the control protein as an index. However, reactivity to dog IgE antigen was observed only for the antibody having the variable region of H5.

Example 2

Expression of Recombinant-Type Dog IgE Antibody (H5 (CCH3-5), X1) in Silkworm

1. Cloning of Recombinant-Type Anti-Dog IgE Antibody into pBM030 Vector

Figure 8:
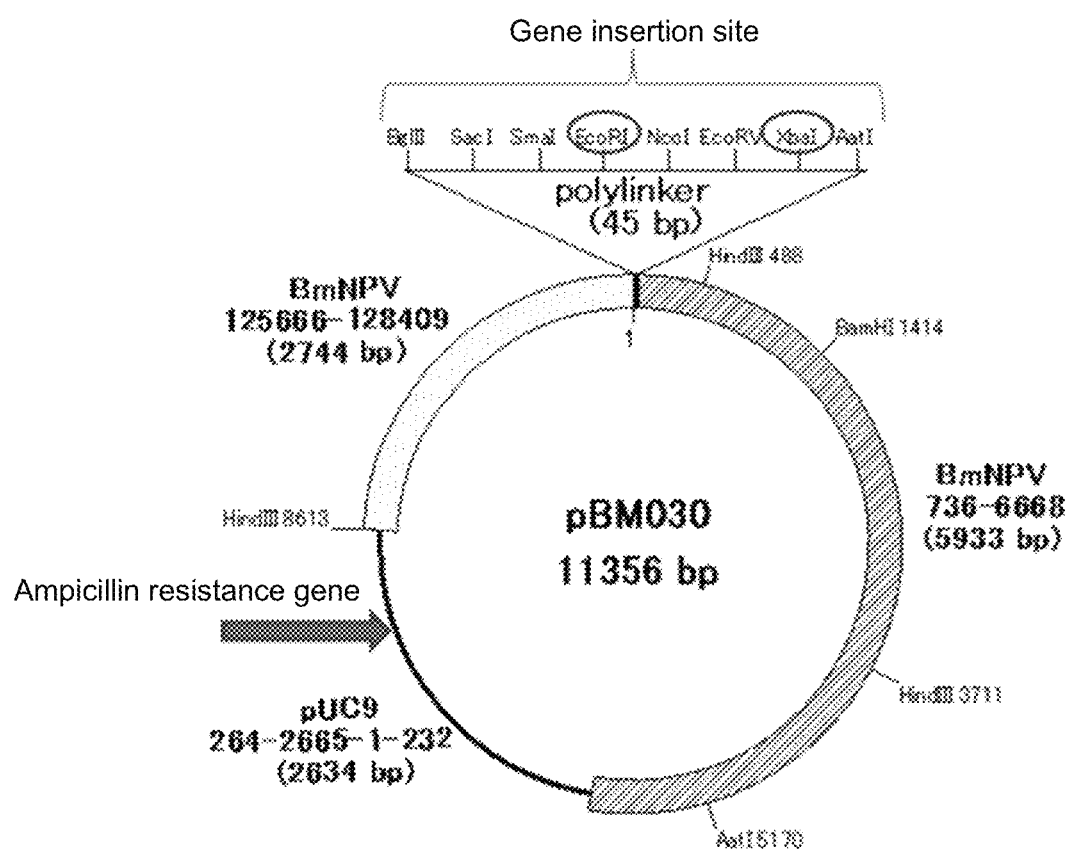
FIG. 8 is a diagram showing a structure of BM030 vector used for the expression of a recombinant type anti-dog IgE antibody in a silkworm.

1) For expression in a silkworm, the recombinant-type anti-dog IgE antibody was cloned into pBM030 vector. In order to introduce each of H5 HVR-rat IgG2b CR, X1 HVR-rat IgG2b CR, H5 KVR-rat IgK CR, and X1 KVR-rat IgK CR between the EcoRI and XbaI recognition sites of the vector, the DNA fragments were each amplified using primers containing the recognition sequence for EcoRI or XbaI (combination of 23/24, 25/24, 26/24, or 27/24), excised with EcoRI and XbaI, phoresed on an agarose gel, and purified using Wizard SV Gel and PCR Clean-up System (#A9282) from Promega Corporation, and used for ligation (FIG. 9A). Takara PrimeSTAR with a low mutation introduction rate was used for PCR reaction. Since the pBM030 vector is as large as 11 kb or more, TaKaRa DNA Ligation Kit LONG (#6024) was used for ligation reaction, and host *Escherichia coli* HST08 Premium effective on long-chain plasmid DNA was used for transformation. The structure of the pBM030 vector used is shown in FIG. 8.

2) Assuming a case where the expression and secretion of each recombinant antibody in a silkworm was poor, a recombinant antibody expression vector containing DNA coding a signal peptide of polyhedron was prepared. Using a signal peptide DNA-containing pBM030 vector (Signal) prepared by Nippon Zenyaku Co., Ltd. as the vector, the DNA fragment of the recombinant antibody from which its signal peptide was excluded was amplified between EcoRI and XbaI by PCR (primers: a combination of 28/24, 29/24, 30/24, or 31/24) for cloning (FIG. 9B).

Figure 9:
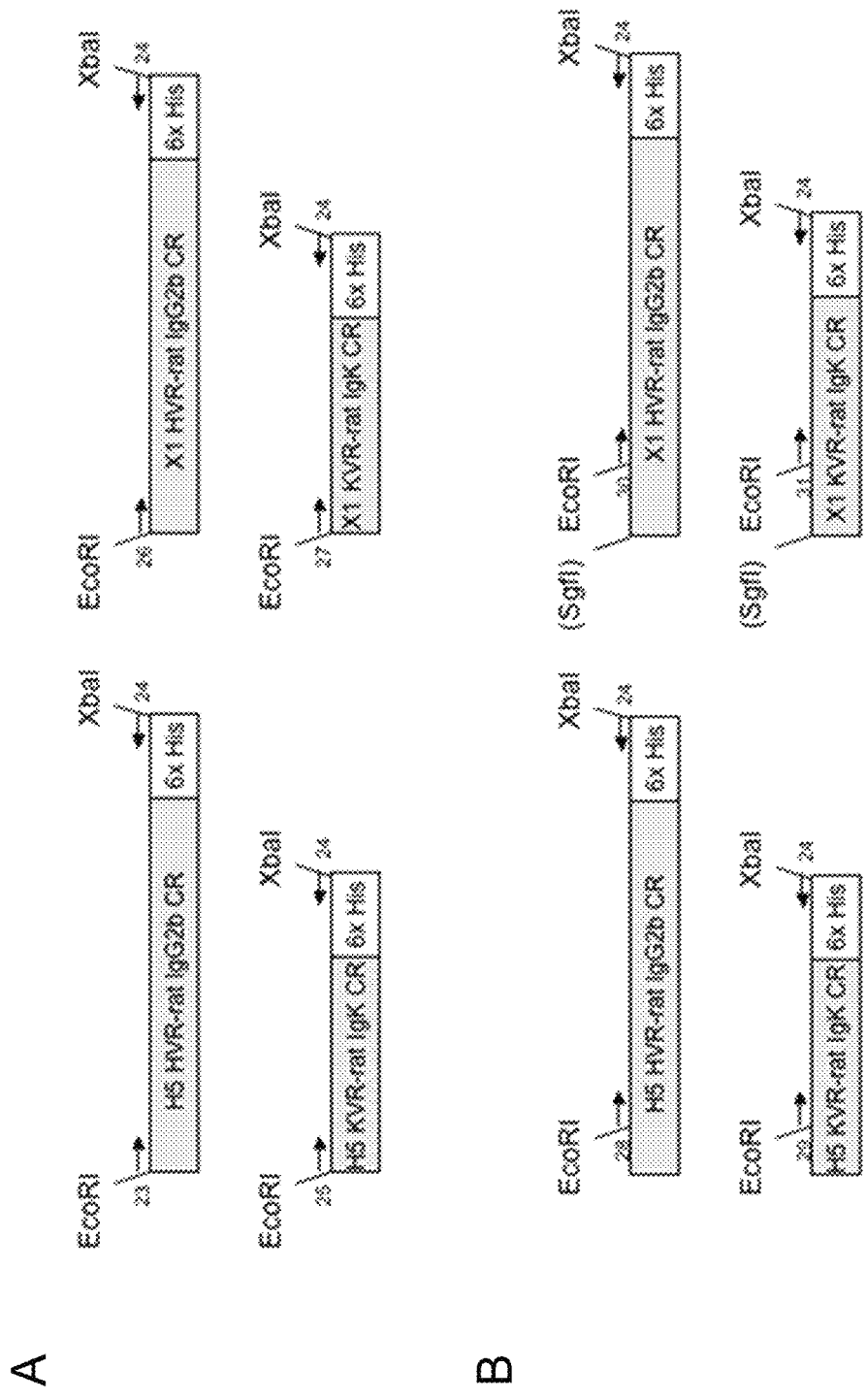
FIG. 9 is a pair of diagrams showing structures of DNAs used for cloning a recombinant type anti-dog IgE antibody into pBM030 vector.

FIG. 9 shows the structure of DNAs used for cloning recombinant-type anti-dog IgE antibodies into the pBM030 vector.

Figure 10:
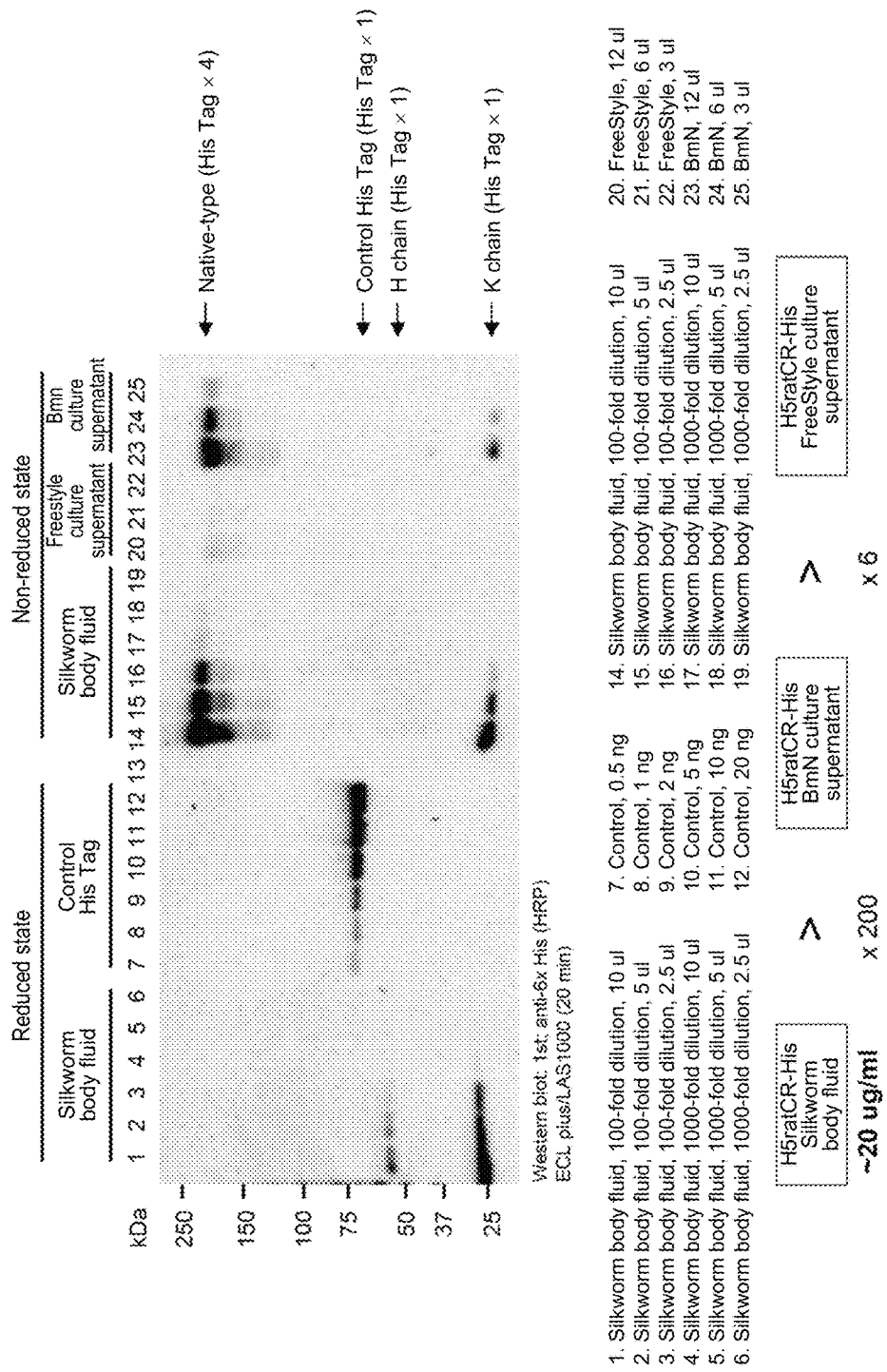
FIG. 10 is a pair of photographs showing the expression level of a recombinant type anti-dog IgE antibody in the BmN cell supernatant and the silkworm body fluid.

2. Comparison of Expression Level of Recombinant-Type Anti-Dog IgE Antibody in BmN Cell Supernatant and Silkworm Body Fluid and Evaluation of Antibody Activity 1) To examine the expression level of recombinant-type anti-dog IgE H5ratCR-His antibody, a silkworm body fluid and culture supernatants of FreeStyle 293F cells and BmN cells diluted to suitable amounts were subjected to separation by SDS-PAGE, and the anti-dog IgE H5ratCR-His recombinant antibody was subjected to Western blot analysis using an anti-6× His (HRP) antibody to perform the rough quantitation of the antibody. To facilitate quantitation, phoresis in a reduced state was also carried out for the silkworm body fluid; however, since the FreeStyle cell culture supernatant is stingy and the BmN cell culture supernatant could not be detected for the band of H-chain due to contaminants, the quantitative comparison of the antibody in these solutions was performed using the intensity of the signal of the native-type antibody in a non-reduced state. The native-type having 2 H and K chains will have 4 His tags. The H5ratCR-His antibody found in the silkworm body fluid and the BmN cell supernatant has excessively expressed K-chains; however, the rough amount of the antibody is about 20 µg/ml for the silkworm body fluid, about 0.1 µg/ml for the BmN cell supernatant, and about 0.02 µg/ml for the FreeStyle supernatant, as an antibody concentration. The results of measuring the antibody expression level are shown in FIG. 10.

Figure 11:
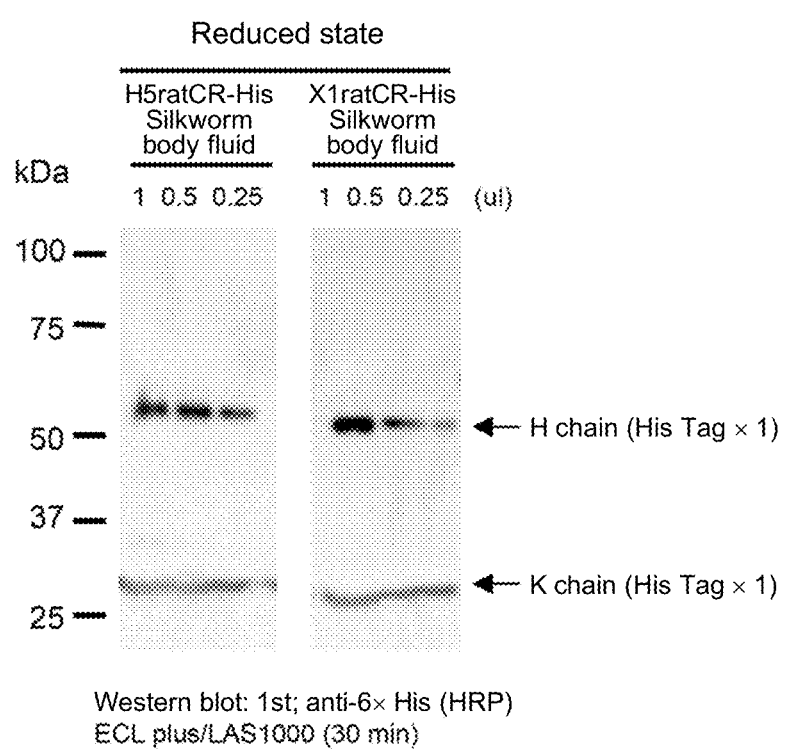
FIG. 11 is a pair of photographs showing the results of Western blot analysis of the amount of antibodies contained in the silkworm body fluid for H5ratCR-His and X1ratCR-His.

The results of similarly analyzing the amount of the antibody contained in the silkworm body fluid for H5ratCR-His and X1ratCR-His by Western blotting are shown in FIG. 11. As shown in FIG. 11, H5ratCR-His and X1ratCR-His were expressed in a comparable level. Expression could not be confirmed in the BmN cell culture supernatant for H5ratCR-His and X1ratCR-His with the signal peptides of polyhedrin.

Figure 12:
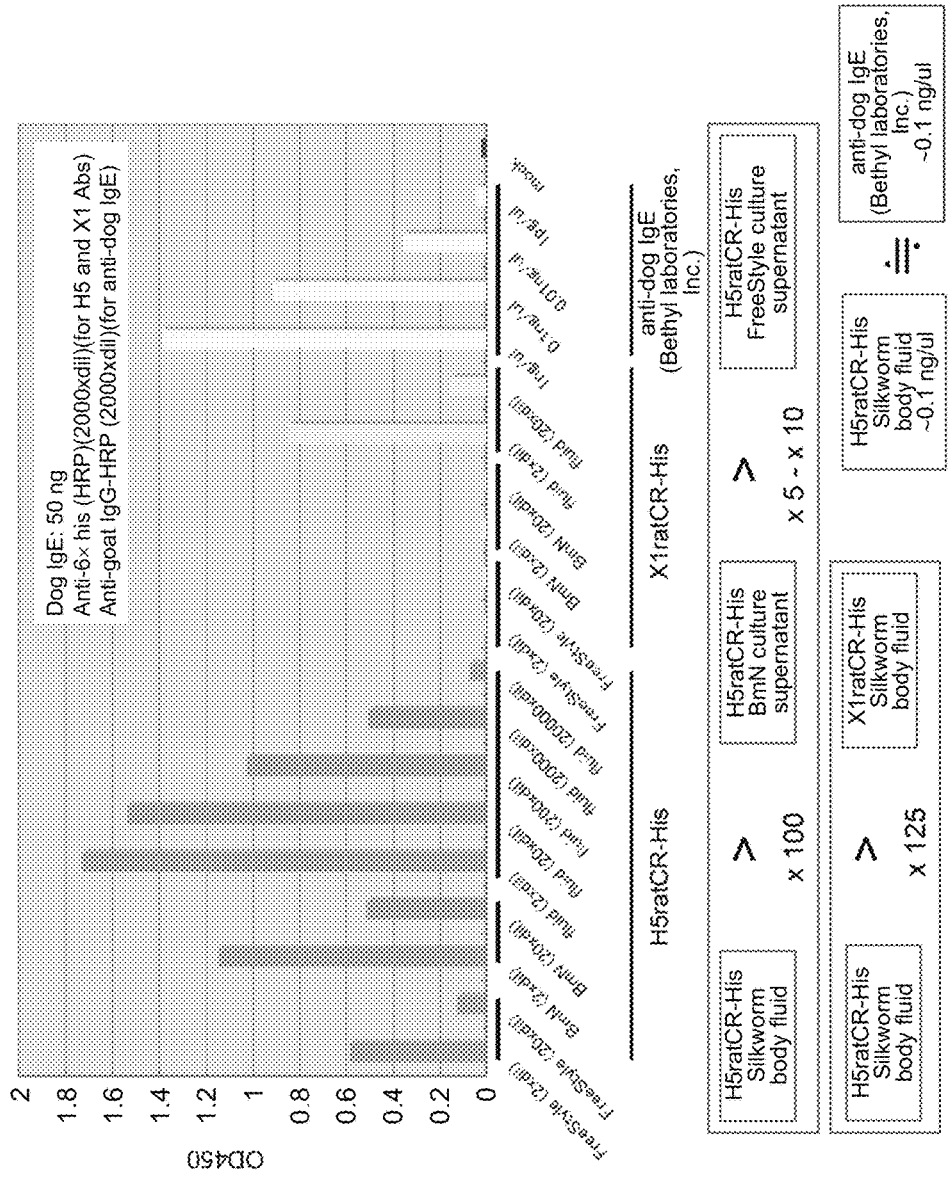
FIG. 12 is a drawing showing the results of ELISA measurement of a recombinant type anti-dog IgE antibody in a BmN cell supernatant and a silkworm body fluid.

2) To evaluate the recombinant antibody activity against dog IgE, suitable amounts of the silkworm body fluid and the FreeStyle 293F cell and BmN cell culture supernatants serially diluted were used to perform an ELISA experiment for H5ratCR-His and X1ratCR-His against dog IgE. As control, another ELISA experiment was simultaneously performed using a goat anti-dog IgE antibody from Bethyl Laboratories, Inc., serially diluted. The results are shown in FIG. 12. As shown in FIG. 12, with H5ratCR-His, comparable color development was observed at 2,000-fold dilution for the silkworm body fluid, at 2-fold dilution for the FreeStyle culture supernatant, and at 20-fold dilution for the BmN cell supernatant. X1ratCR-His was observed to result in color development only for the silkworm body fluid at 2-fold dilution and was 100 times or more weaker in activity than H5ratCR-His. The recombinant antibody was analyzed using anti-6× His (HRP) with the anti-dog IgE antibody activity analyzed using anti-goat IgG (HRP), not enabling direct comparison; however, H5ratCR-His in the silkworm body fluid diluted 200-fold, and the anti-dog IgE antibody at a concentration of 0.1 ng/µL resulted in comparable color development, and both of them had a concentration of 0.1 ng/µL.

Figure 13:
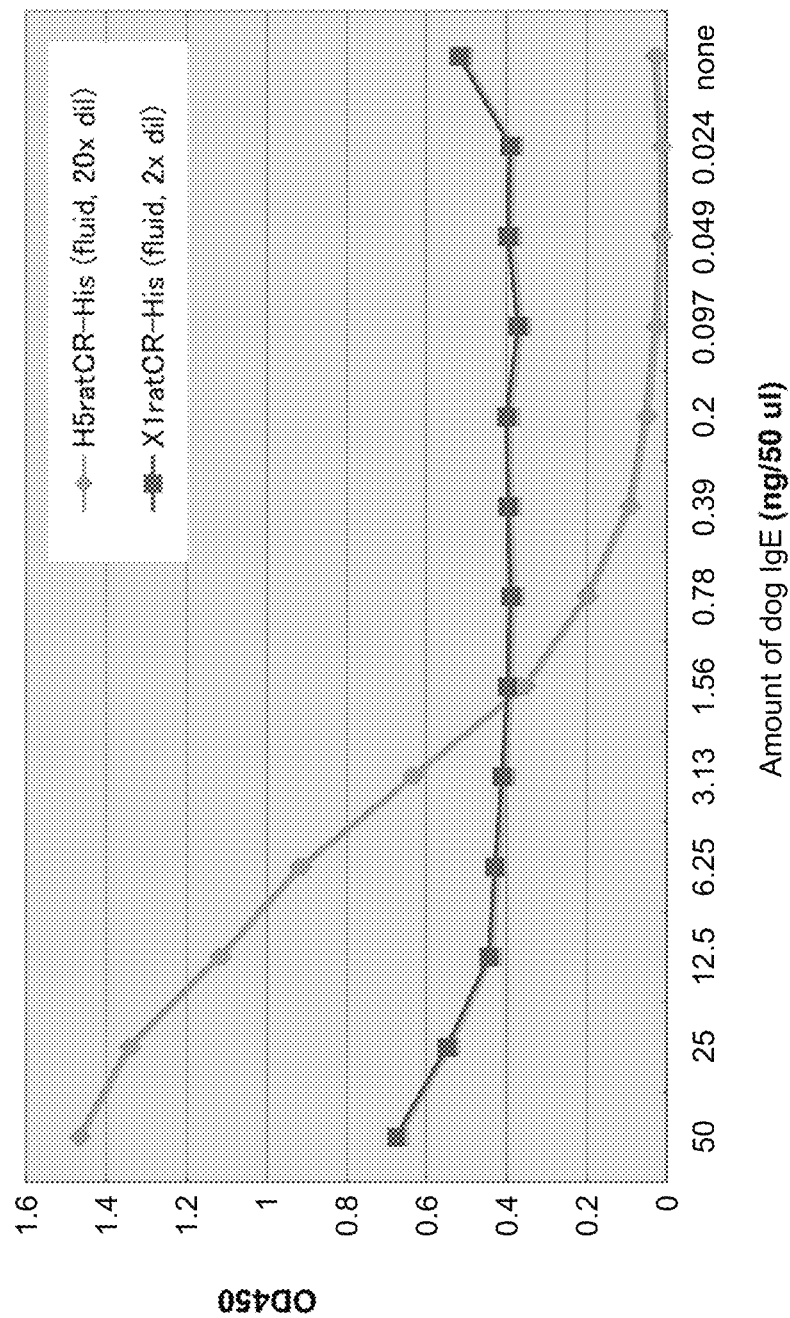
FIG. 13 is a graph showing the reactivity of an anti-IgE antibody expressed in the silkworm body fluid to dog IgE.

3) To confirm the reactivity of the anti-IgE antibody expressed in the silkworm body fluid to dog IgE, an ELISA experiment was carried out using a plate on which dog IgE from Bethyl Laboratories, Inc., serially diluted from 50 ng/well (50 µL) to 24 pg/well was immobilized. The results are shown in FIG. 13. As shown in FIG. 13, H5ratCR-His exhibited reactivity depending on the antigen level; however, X1ratCR-His had a high background value in a well containing no antigen. Nonspecific adsorption due to the influence of contaminating protein was probably present for a sample of the silkworm body fluid at 2-fold dilution; however, in any case, the affinity of X1ratCR-His to dog IgE was lower than that of H5ratCR-His.

Example 3

Purification of Anti-Dog IgE Recombinant Antibody (H5_ratFc-HisTag) from Silkworm Body Fluid (1)

(1) Purification of Anti-Dog IgE Recombinant Antibody Using HisTag and Ion-Exchange Column As a pilot test for recombinant antibody purification, HisTag purification by batch adsorption of TALON resin was carried out using 1 ml of the silkworm body fluid. The silkworm body fluid was used by 10-fold dilution with PBS because of having high viscosity and reacted with 50 µl (column volume) of TALON resin. Washing was carried out 3 times with a 10 column volume (500 µl) of PBST, and elution was carried out 8 times using PBST containing 4 column volume (200 µl) of 250 mM imidazole.

The elution fraction (about 1.6 ml) was pooled, and when the recovery rate was estimated by Western blotting, nearly 80% of the input was recovered. When purity was confirmed by silver staining, the antibody and contaminating proteins having lower molecular weights than that were confirmed. The contaminating proteins were confirmed at the same places by electrophoresis under reduced conditions and thus were probably not degradation products but contaminants derived from the silkworm body fluid as a material.

First, to remove these contaminating proteins, purification using Protein G agarose was studied. However, as the Fc region of the anti-dog IgE recombinant antibody, that of rat IgG2b was used, and thus its binding property to Protein G was not so high. Protein G has a high binding property to rat IgG2b compared to Protein A. However, as a result, the recombinant antibody remaining in an unbound fraction was abundantly observed, and the recovery rate of the antibody was roughly 25% of the HisTag purified product. Purification using Protein G was probably not suited to practical use in terms of the recovery rate, and there was also concern that the purification adversely affected the antibody activity because of using an acid for its elution.

From the above, the HisTag-purified recombinant antibody was further subjected to purification using an ion-exchange column to examine an improvement in purity. A HiTrap CM sepharose (1 ml) column was used for purification. Roughly 1 ml of the elution fraction obtained by HisTag purification was added to the ion-exchange column. Elution was carried out with a concentration gradient from 100 mM to 1 M NaCl using 100 mM Na—$PO_4$ buffer (pH 6.0). Using absorption at 280 nm as an index, a fraction containing protein was identified, and purity was confirmed by electrophoresis and silver staining. The protein solution obtained was also pooled (about 2.5 ml). In addition, it was concentrated 10-fold (250 μl) by utilizing HisTag, and purity was confirmed by silver staining.

Figure 14:
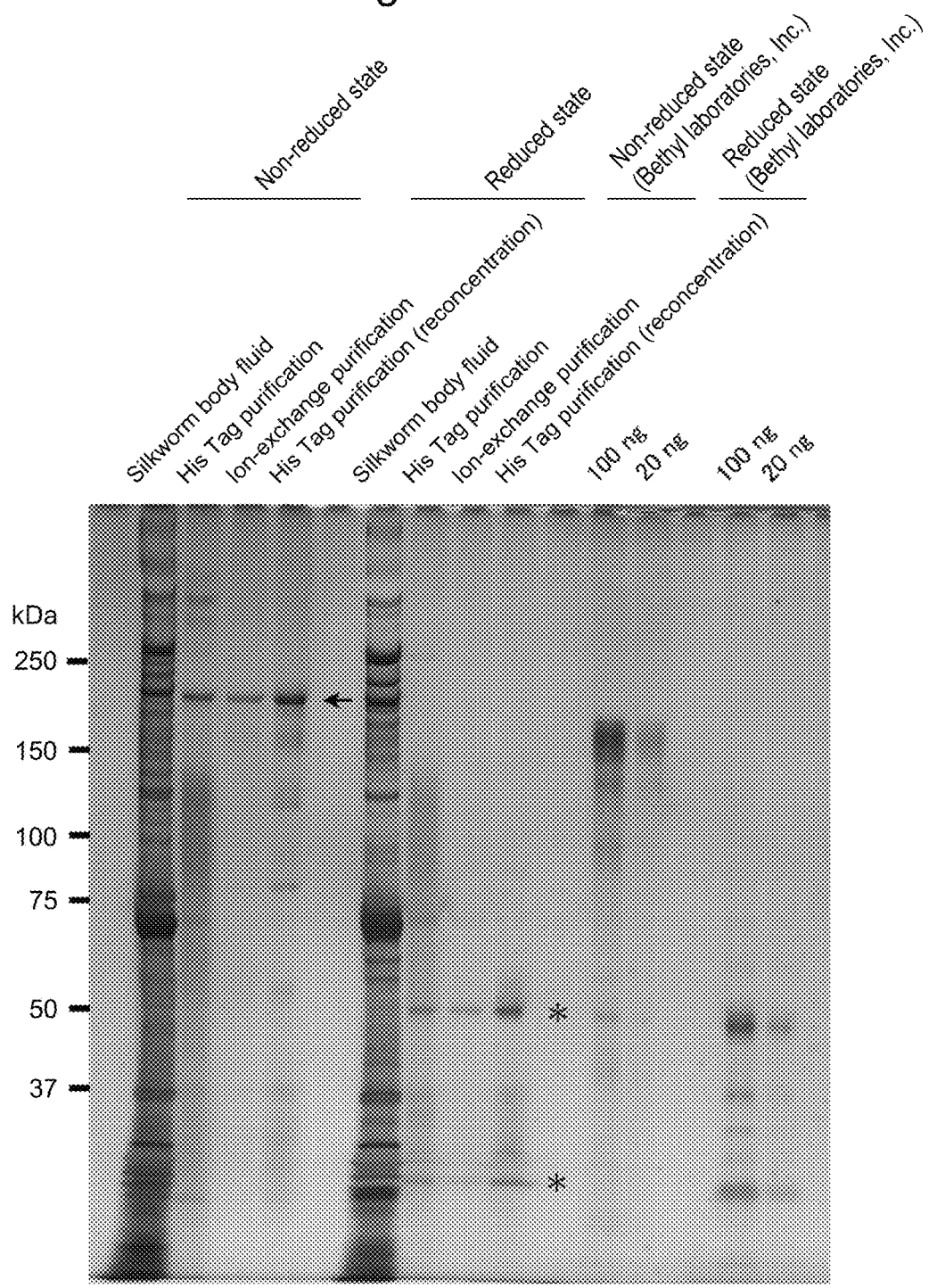
FIG. 14 is a photograph showing the results of silver staining of an anti-dog IgE recombinant antibody purified from the silkworm body fluid.

The results are shown in FIG. 14. FIG. 14 shows the results of subjecting the silkworm body fluid diluted 1,000-fold (1 μl), the HisTag-purified product (1.2 μl), the ion-exchange purified product (2 μl), and the HisTag reconcentration fraction (2 μl) to electrophoresis under non-reduced and reduced conditions, followed by silver staining. In FIG. 14, the arrow indicates the recombinant antibody, and * indicates its heavy chain and light chain. As shown in FIG. 14, in the concentrated sample, contaminating proteins were slightly observed in the low molecular region of around 30 kDa; however, the sample could be purified to an extent almost comparable to the antibody from Bethyl Laboratories, Inc., phoresed as a control. When the protein content was quantitated by Western blotting, roughly 25 μg of the antibody was recovered after ion-exchange column purification from 1 ml of the silkworm body fluid (about 30 mg of protein). From this, it is estimated that purification using the remaining total amount (about 45 ml) of the silkworm body fluid supplied by Nippon Zenyaku Co., Ltd. enables the recovery of the antibody on the order of 1 mg.

(2) Activity Evaluation of Purified Anti-Dog IgE Recombinant Antibody

Figure 15:
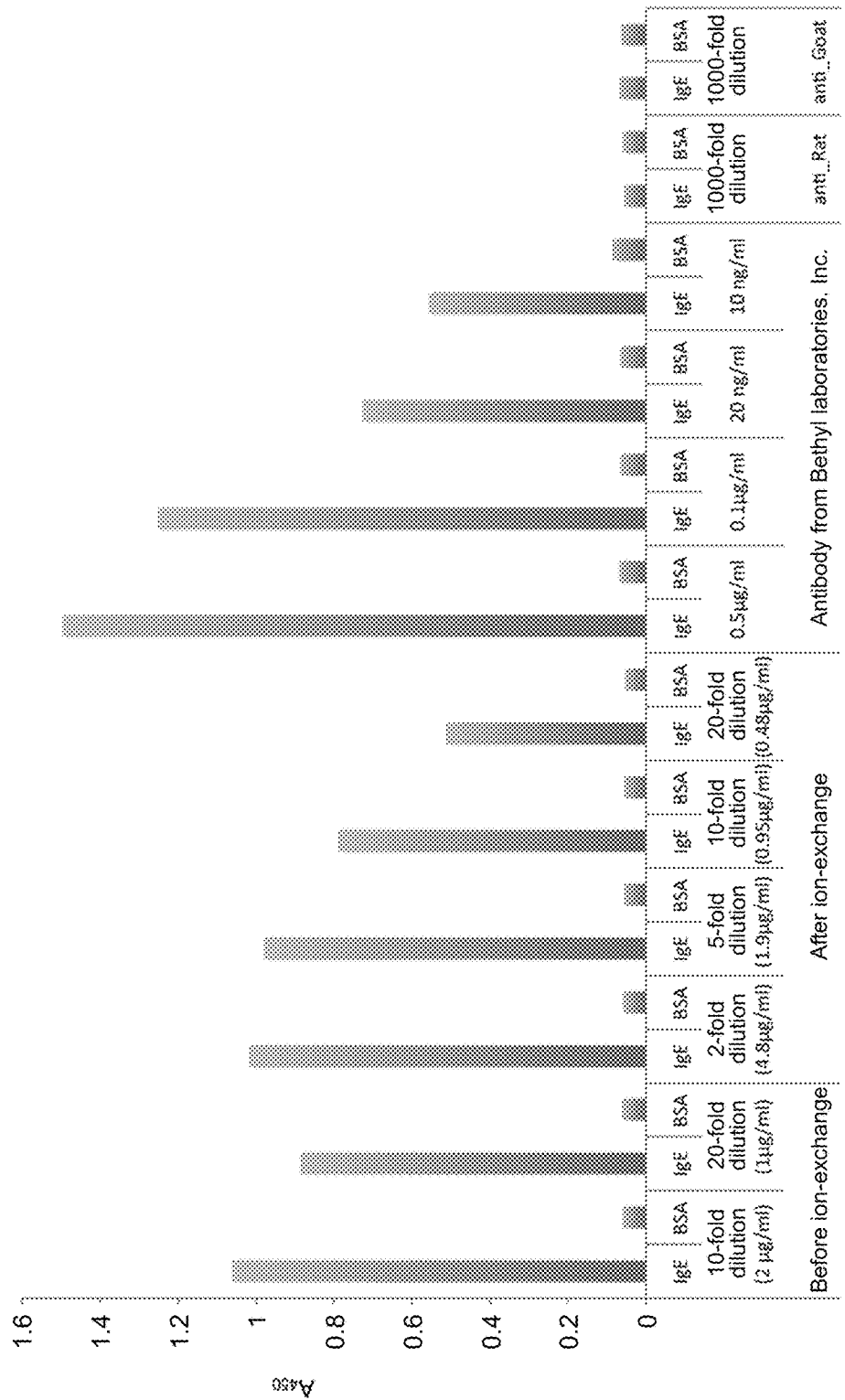
FIG. 15 is a graph showing the results of the reactivity test of an anti-dog IgE recombinant antibody purified from a silkworm body fluid by an ELISA method.

The reactivity of the purified recombinant antibody to dog IgE was examined. A 10-fold and 20-fold diluted sample before addition to an ion-exchange column and a 2- to 20-fold serially diluted (4.8 to 0.48 μg/ml) elution fraction from the ion-exchange column were each added in an amount of 100 μl to 50 ng of dog IgE (Bethyl Laboratories, Inc.) or BSA bound to an ELISA plate. As a control, an anti-dog IgE antibody from Bethyl Laboratories, Inc. was added to 0.5 to 0.01 μg/ml. Detection was carried out by 1,000-fold diluting anti-rat IgG-HRP or anti-goat IgG-HRP antibody with PBST/casein and using TMBZ as a substrate. To confirm non-specific reaction by the secondary antibody, a sample containing no primary antibody was also analyzed. The results are shown in FIG. 15. FIG. 15 shows the results of confirming reactivity with the recombinant antibody after adding 50 ng of dog IgE or BSA as an antigen to an ELISA plate for immobilization. As shown in FIG. 15, the specific binding of the recombinant antibody to dog IgE was confirmed. The ion-exchange purified recombinant antibody was on the order of roughly 1/3 in activity in the ELISA compared to the antibody from Bethyl Laboratories, Inc. although the secondary antibody was different. When the diluted silkworm body fluid was used, the activity in the ELISA was also on the order of 1/3 compared to that for the antibody from Bethyl Laboratories, Inc.; thus, it is probable that the risk of activity loss during purification process remains minimal. It was also confirmed that no non-specific binding of the secondary antibody was observed.

Conclusion

The combination of purifications with HisTag and ion-exchange column enabled the purification of the anti-dog IgE recombinant antibody (H5_ratFc-HisTag) to an extent comparable to that of the commercial antibody. From 1 ml of the silkworm body fluid, on the order of 25 μg of the antibody purified to high purity was recovered as a final product.

The antibody was also estimated to be on the order of 1/3 in activity compared to that for the antibody from Bethyl Laboratories, Inc.

Example 4

Purification of Anti-Dog IgE Recombinant Antibody (H5_ratFc-HisTag) from Silkworm Body Fluid (2)

(1) Purification of Anti-Dog IgE Recombinant Antibody Using HisTag and Ion-Exchange Column A large amount of the anti-dog IgE recombinant antibody from the silkworm body fluid was prepared in reference to the method by which the purification of the antibody was studied in the pilot test. The silkworm body fluid diluted 10-fold (about 500 ml) was reacted with 2.5 ml of TALON resin by batch adsorption and then poured into a polypropylene column to recover the resin. The recovered resin was washed 3 times with PBST (20 ml), and elution was performed 10 times with 4 ml of PBST containing 250 mM imidazole. The recovered protein was subjected to SDS-PAGE, and the band thereof was confirmed by silver staining; as a result, the majority was eluted at the first elution (Fr. 1) as in the above.

Fr. 1 in which the majority of the recombinant antibody was recovered was subjected to Western blotting, and its concentration was estimated based on the signal intensity of a control protein; as a result, the concentration was estimated to be on the order of roughly 200 μg/ml and the amount recovered was estimated to be about 800 μg per 4 ml.

The protein (Fr. 1) obtained by HisTag purification was further purified by ion-exchange chromatography using a CM-sepharose column. Purification was carried out by connecting HiTrap CM sepharose (1 ml: General Electric Company) to an AKTA prime chromatography system. Since the addition of a sample to the column was performed using a 2-ml sample loop, 1.8 ml as about half of the amount of Fr. 1 was used for one purification, and the purification was carried out 2 times. The remaining about 400 μL was subjected to chilled storage for subsequent evaluation. As buffer, 100 mM Na—$PO_4$ buffer (pH 6.0) was used, and elution was carried out with a concentration gradient from 100 mM to 1 M NaCl. Electrophoresis was performed using absorption at 280 nm as an index, and purity was confirmed by silver staining.

Figure 16:
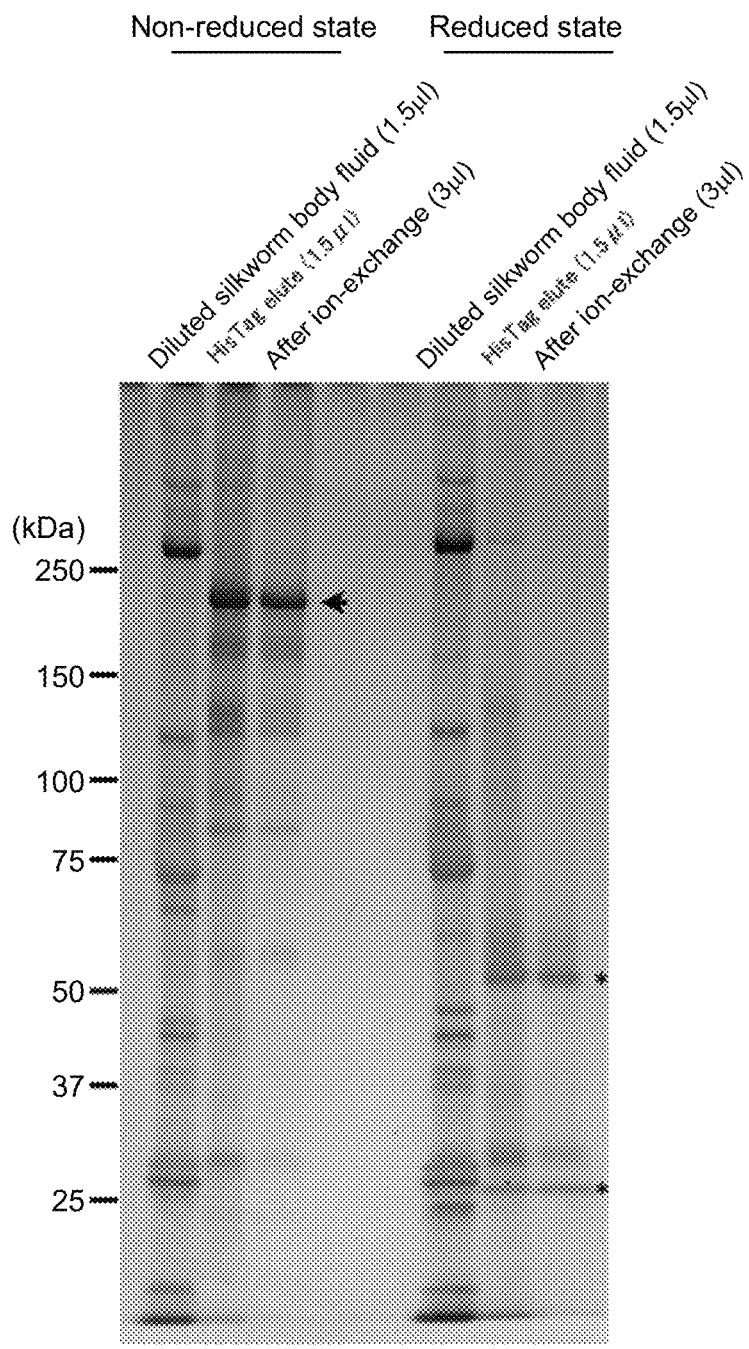
FIG. 16 is a photograph showing the results of silver staining of an anti-dog IgE recombinant antibody purified from a silkworm body fluid.

The results are shown in FIG. 16. FIG. 16 shows the results of subjecting the silkworm body fluid diluted 2,000-fold (1.5 μl), the HisTag-purified product (1.5 μl), and the ion-exchange purified product (3 μl) to electrophoresis under non-reduced and reduced conditions, followed by silver staining. In FIG. 16, the arrow indicates the recombinant antibody, and * indicates its heavy chain and light chain. In the concentrated sample, contaminating proteins were slightly observed in the low molecular region of around 30 kDa; however, the recombinant antibody could be purified to a purity comparable to that obtained in the pilot test (FIG. 16). SDS-PAGE was performed, followed by estimating the concentration by Western blotting based on the signal intensity of the control protein; as a result, the concentration was estimated to be roughly 80 μg/ml, and on the order of 560 μg was recovered as a whole (about 7 ml).

(2) Binding Evaluation of Purified Anti-Dog IgE Recombinant Antibody by ELISA Assay 50 ng of Dog IgE (Bethyl Laboratories, Inc.) or BSA was added to an ELISA plate and bound thereto at 4° C. overnight. After removing the supernatant, washing was carried out one time with 200 μL of PBST, and 200 μl of PBST containing 1× casein (Vector laboratories, Inc.) was added, followed by blocking at 37° C. for 1 hour. The resultant was washed 3 times with 200 μl of PBST, followed by adding 100 μl of the silkworm body fluid (diluted 50-fold or 100-fold), the HisTag purified product (diluted 10-fold or 20-fold), or the ion-exchange purified product (diluted 5-fold, 10-fold, 20-fold, or 50-fold). As a control, the anti-dog IgE antibody from Bethyl Laboratories, Inc. was adjusted to 0.5 μg to 10 ng/ml and added in an amount of 100 After reaction at 37° C. for 90 minutes, the resultant was washed 3 times with 200 μl of PBST, followed by 1,000-fold diluting an HRP-labeled anti-rat or anti-goat secondary antibody and adding 100 μl thereof. After reaction at 37° C. for 90 minutes, the resultant was washed 3 times with 200 μl of PBST, followed by adding 100 μl of a citrate buffer solution using TMBZ as a substrate. After reaction at room temperature for 10 to 15 minutes, 50 μl of 2N sulfuric acid was added to stop the reaction. A SpectraMax M2 plate reader from Molecluar Devices, LLC. was used for measuring absorption at 450 nm.

Figures 1, 17:
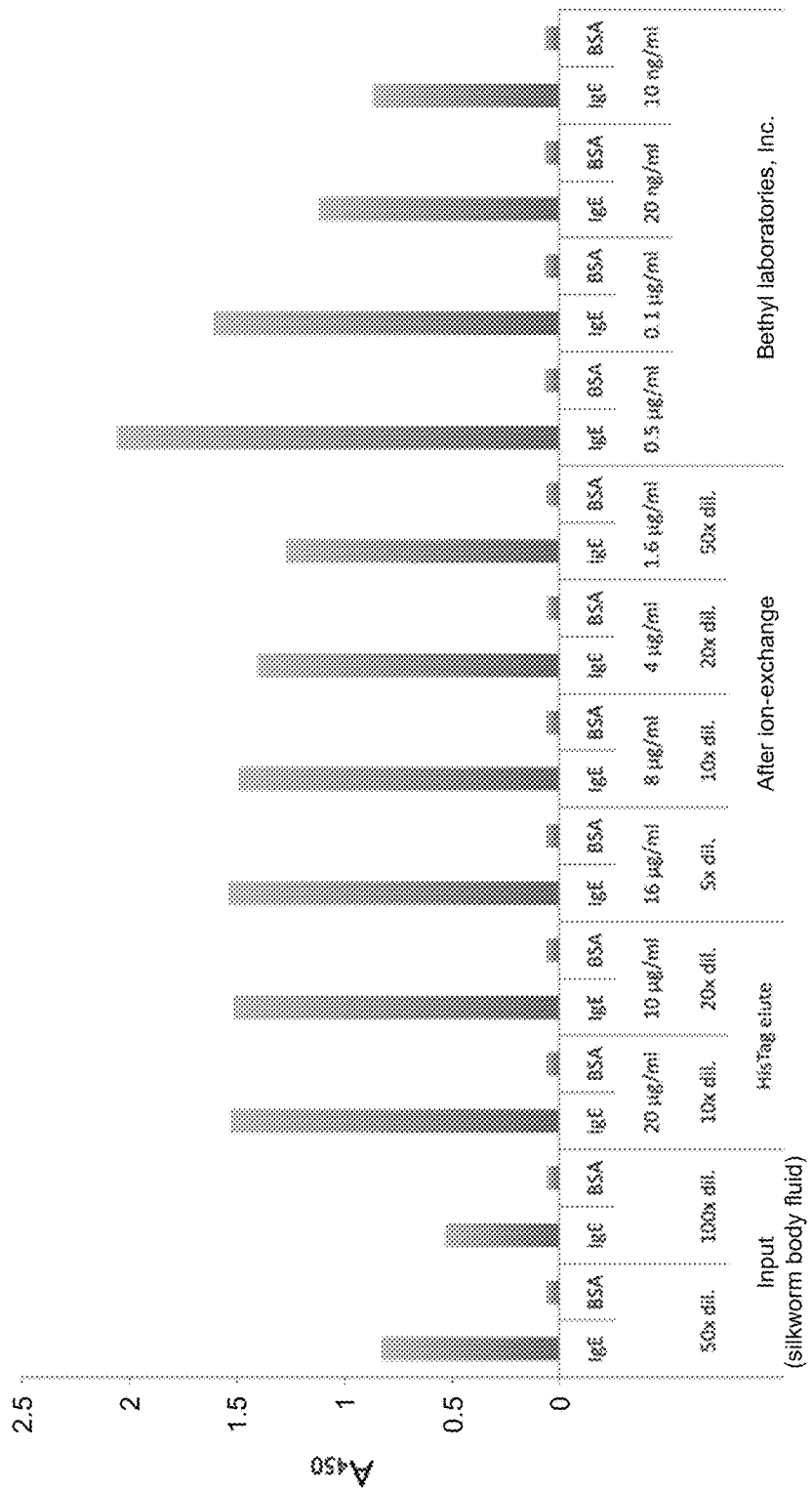
Figures 2, 17:
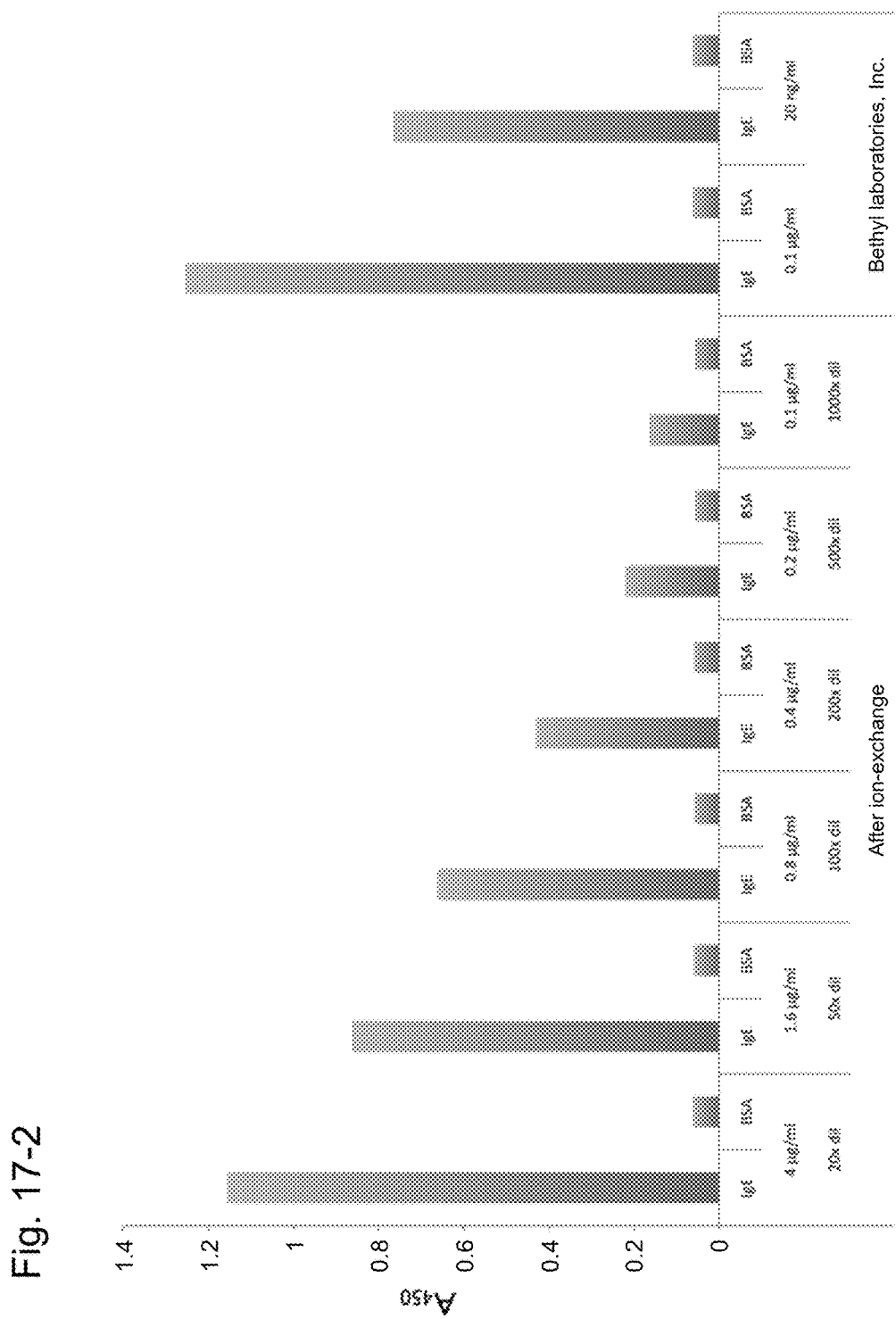

The results are shown in FIGS. 17-1 and 17-2. FIG. 17-1 shows the results of examining the silkworm body fluid, the HisTag eluate, and the ion-exchanged product (5- to 50-fold dilution). The reaction with TMBZ was conducted for 15 minutes. FIG. 17-2 shows the results of studying the ion-exchanged purified product by further proceeding with dilution (20- to 1,000-fold dilution). The reaction with TMBZ was conducted for 10 minutes. The prepared recombinant antibody exhibited a high binding activity even at 50-fold dilution. Thus, as a result of performing ELISA assay by further proceeding with dilution, a significant signal was confirmed even at 1,000-fold dilution. As a result of ELISA assay using a comparable amount of protein from the HisTag purified product and the ion-exchanged sample, no difference was observed in the absorption value at 450 nm; thus, activity loss during the purification process probably minimally occurred.

(3) Study on Storage Method

Figure 18:
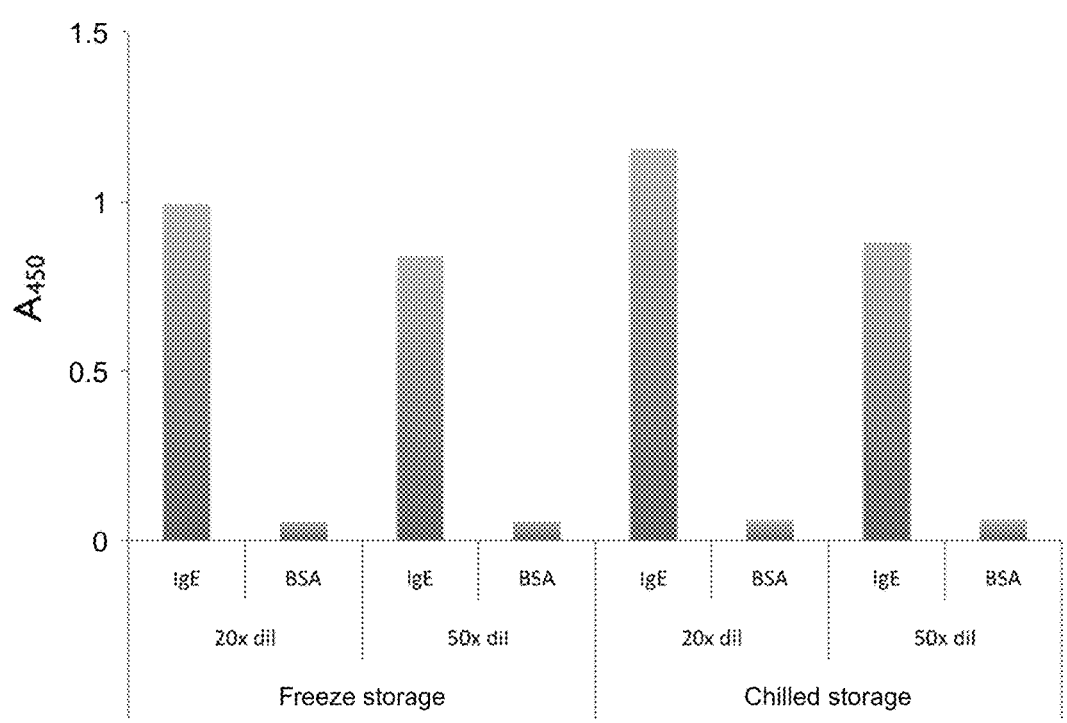
FIG. 18 is a graph showing the influence of freezing and thawing on the reactivity of an anti-dog IgE recombinant antibody.

Effects of the freezing and thawing of the antibody solution on reactivity with the antigen were studied. The antibody solution was frozen in a small amount at −80° C. overnight, thawed on the following day, diluted 20 times or 50 times, and subjected to ELISA assay using 50 ng of dog IgE or BSA. As a control, the antibody solution stored at 4° C. was used. Detection was carried out using an HRP-labeled rat IgG secondary antibody and TMBZ as a substrate. Two sets of ELISA assays were performed for each dilution, and reaction with TMBZ was conducted for 10 minutes. The results are shown in FIG. 18. FIG. 18 shows the average value of the 2 sets of experiments. As shown in FIG. 18, the reactivity of the antibody subjected one time to freezing and thawing exhibited no significant reduction compared to that of the antibody subjected to chilled storage.

CONCLUSION

As a result of performing purification using HisTag and ion-exchange column from about 50 ml of the silkworm body fluid, 7 ml of a 80 μg/ml antibody solution was finally prepared, and about 560 μg of the recombinant antibody could be obtained. The binding activity of the purified antibody to dog IgE was evaluated by ELISA assay; as a result, a significant signal was confirmed even when the antibody diluted about 1,000-fold was used. As a result of examining the reactivity of the antibody subjected to freezing and thawing to the antigen, freezing and thawing did not greatly damage the binding activity.

INDUSTRIAL APPLICABILITY

The use of the DNAs encoding the heavy-chain variable region and the light-chain variable region of the anti-dog IgE antibody according to the present invention enables the preparation of an anti-dog IgE antibody as a complete antibody. The resultant anti-dog IgE antibody can be used, for example, for treating an allergic disease in dogs.

SEQUENCE LISTING FREE TEXT

SEQ ID NOS: 13 to 16 Synthesis
SEQ ID NOS: 17 to 51 Primers

All publications, patents, and patent applications cited in the present specification are intended to be incorporated herein by reference in their entirety.

---

The invention claimed is:

1. An anti-dog IgE monoclonal antibody which binds to dog IgE or a functional fragment thereof which binds to dog IgE, comprising a heavy-chain variable region consisting of the amino acid sequence represented by SEQ ID NO: 2 and a light-chain variable region consisting of the amino acid sequence represented by SEQ ID NO: 4, wherein said functional fragment thereof which binds to dog IgE is selected from the group consisting of Fab, Fab', F(ab')$_2$, disulfide-stabilized Fv (dsFv), dimerized V region (diabody), and single chain Fv (scFv).

2. An anti-dog IgE monoclonal antibody which binds to dog IgE or a functional fragment thereof which binds to dog IgE, comprising a heavy-chain variable region consisting of the amino acid sequence represented by SEQ ID NO: 6 and a light-chain variable region consisting of the amino acid sequence represented by SEQ ID NO: 8, wherein said functional fragment thereof which binds to dog IgE is selected from the group consisting of Fab, Fab', F(ab')$_2$, disulfide-stabilized Fv (dsFv), dimerized V region (diabody), and single chain Fv (scFv).

3. The anti-dog IgE monoclonal antibody which binds to dog IgE or the functional fragment thereof which binds to dog IgE according to claim 1, wherein the class of the antibody is IgG, IgA, IgE, or IgM.

4. The anti-dog IgE monoclonal antibody which binds to dog IgE or the functional fragment thereof which binds to dog IgE according to claim 3, wherein the subclass of the antibody is IgG1, IgG2, IgG3, or IgG4.

5. The anti-dog IgE monoclonal antibody which binds to dog IgE or the functional fragment thereof which binds to dog IgE according to claim 1, being the functional fragment thereof which binds to dog IgE.

6. A polypeptide which is a heavy-chain variable region of an anti-dog IgE antibody, consisting of the amino acid sequence represented by SEQ ID NO: 2 or 6.

7. A polypeptide which is a light-chain variable region of an anti-dog IgE antibody, consisting of the amino acid sequence represented by SEQ ID NO: 4 or 8.

8. A reagent for detecting a dog allergic disease, comprising the anti-dog IgE monoclonal antibody which binds to dog IgE or the functional fragment thereof which binds to dog IgE according to claim 1.

9. The anti-dog IgE monoclonal antibody which binds to dog IgE or the functional fragment thereof which binds to dog IgE according to claim 2, wherein the class of the antibody is IgG, IgA, IgE, or IgM.

10. The anti-dog IgE monoclonal antibody which binds to dog IgE or the functional fragment thereof which binds to dog IgE according to claim 9, wherein the subclass of the antibody is IgG1, IgG2, IgG3, or IgG4.

11. The anti-dog IgE monoclonal antibody which binds to dog IgE or the functional fragment thereof which binds to dog IgE according to claim 2, being the functional fragment thereof which binds to dog IgE.

12. A reagent for detecting a dog allergic disease, comprising the anti-dog IgE monoclonal antibody which binds to dog IgE or the functional fragment thereof which binds to dog IgE according to claim 2.

13. A polynucleotide encoding a heavy-chain variable region of an anti-dog IgE antibody, consisting of the DNA sequence represented by SEQ ID NO: 1 or 5.

14. A polynucleotide encoding a light-chain variable region of an anti-dog IgE antibody, consisting of the DNA sequence represented by SEQ ID NO: 3 or 7.

15. A vector comprising at least one of the polynucleotide according to claim 13 or the polynucleotide according to claim 14.

16. A cell comprising the vector according to claim 15.

17. A silkworm comprising the vector according to claim 15.

18. A method for producing an anti-dog IgE antibody, comprising: linking DNA encoding a heavy-chain variable region of an anti-dog IgE antibody, consisting of the DNA sequence represented by SEQ ID NO: 1 to DNA encoding a heavy-chain constant region of the antibody; linking DNA encoding a light-chain variable region of an anti-dog IgE antibody, consisting of the DNA sequence represented by SEQ ID NO: 3 to DNA encoding a light-chain constant region of the antibody; inserting the resultant DNA constructs into an expression vector, transforming a host cell or a host animal with the vector, and producing an antibody using the host cell or the host animal.

19. A method for producing an anti-dog IgE antibody, comprising: linking DNA encoding a heavy-chain variable region of an anti-dog IgE antibody, consisting of the DNA sequence represented by SEQ ID NO: 5 to DNA encoding a heavy-chain constant region of the antibody; linking DNA encoding a light-chain variable region of an anti-dog IgE antibody, consisting of the DNA sequence represented by SEQ ID NO: 7 to DNA encoding a light-chain constant region of the antibody; inserting the resultant DNA constructs into an expression vector, transforming a host cell or a host animal with the vector, and producing an antibody using the host cell or the host animal.

20. The method according to claim 19, wherein the DNA encoding a heavy-chain constant region of the antibody consists of the DNA sequence represented by SEQ ID NO: 9 and the DNA encoding a light-chain constant region of the antibody consists of the DNA sequence represented by SEQ ID NO: 11.

21. The method for producing an anti-dog IgE antibody according to claim 18, wherein the host animal is a silkworm.

22. A method for detecting a dog allergic disease, comprising measuring IgE antibody in the blood, serum, or plasma collected from a dog using the anti-dog IgE monoclonal antibody which binds to dog IgE or the functional fragment thereof which binds to dog IgE according to claim 1.

23. The method for producing an anti-dog IgE antibody according to claim 19, wherein the host animal is a silkworm.

24. A method for detecting a dog allergic disease, comprising measuring IgE antibody in the blood, serum, or plasma collected from a dog using the anti-dog IgE monoclonal antibody which binds to dog IgE or the functional fragment thereof which binds to dog IgE according to claim 2.

* * * * *

SEQUENCE LISTING

```
<160> NUMBER OF SEQ ID NOS: 51

<210> SEQ ID NO 1
<211> LENGTH: 411
<212> TYPE: DNA
<213> ORGANISM: Mus musculus

<400> SEQUENCE: 1
atggaatgga gctggatctt tctcttcctc ctgtcaggaa ctacaggtgt ccactctgag      60
atccagctgc agcagtctgg acctgagctg gtgaagcctg gggcttcagt gaaggtttcc     120
tgcaaggctt ctggttactc attcactgac taccacatat actgggtgag gcagagccat     180 gaaagagcc tagagtggat tggatatatt gatccttaca aaggtggtac tacctacaac     240
```

```
cataatttca agggcaaggc ctcattgact gttgacaagt cctccagcac agccttcatg      300
catctcaaca gcctaacatc tgatgactct gcagtctatt actgtgcgag agaggctggc      360
tataggtacg acaattactg gggccaaggg actctggtca ctgtctctgc a               411
```

<210> SEQ ID NO 2
<211> LENGTH: 137
<212> TYPE: PRT
<213> ORGANISM: Mus musculus

<400> SEQUENCE: 2

```
Met Glu Trp Ser Trp Ile Phe Leu Phe Leu Leu Ser Gly Thr Thr Gly
1               5                   10                  15

Val His Ser Glu Ile Gln Leu Gln Gln Ser Gly Pro Glu Leu Val Lys
            20                  25                  30

Pro Gly Ala Ser Val Lys Val Ser Cys Lys Ala Ser Gly Tyr Ser Phe
        35                  40                  45

Thr Asp Tyr His Ile Tyr Trp Val Arg Gln Ser His Glu Lys Ser Leu
    50                  55                  60

Glu Trp Ile Gly Tyr Ile Asp Pro Tyr Lys Gly Gly Thr Thr Tyr Asn
65                  70                  75                  80

His Asn Phe Lys Gly Lys Ala Ser Leu Thr Val Asp Lys Ser Ser Ser
                85                  90                  95

Thr Ala Phe Met His Leu Asn Ser Leu Thr Ser Asp Asp Ser Ala Val
            100                 105                 110

Tyr Tyr Cys Ala Arg Glu Ala Gly Tyr Arg Tyr Asp Asn Tyr Trp Gly
        115                 120                 125

Gln Gly Thr Leu Val Thr Val Ser Ala
    130                 135
```

<210> SEQ ID NO 3
<211> LENGTH: 393
<212> TYPE: DNA
<213> ORGANISM: Mus musculus

<400> SEQUENCE: 3

```
atgaagttgc ctgttaggct gttggtgctg atgttctgga ttcctgcttc cagcagtgat      60
gttgtgatga cccaaactcc actctccctg cctgtcagtc ttggagatca agcctccatt      120
tcttgcagat ctagtcagag ccttgtacac agtaatggaa acacctattt acattggtac      180
ctgcagaagg caggccagtc tccaaagctc ctgatctaca agtttccaa ccgattttct       240 ggggtcccag acaggttcag tggcagtgga tcagggacag atttcacact caagatcagc      300
agagtggagg ctgaggatct gggagtttat ttctgctctc aaagtacaca tgttccgtgg      360
acgttcggtg aggcaccaa gctggaaatc aaa                                    393
```

<210> SEQ ID NO 4
<211> LENGTH: 131
<212> TYPE: PRT
<213> ORGANISM: Mus musculus

<400> SEQUENCE: 4

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45
```

Val His Ser Asn Gly Asn Thr Tyr Leu His Trp Tyr Leu Gln Lys Ala
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
             100                 105                 110

Ser Gln Ser Thr His Val Pro Trp Thr Phe Gly Gly Gly Thr Lys Leu
         115                 120                 125

Glu Ile Lys
    130

<210> SEQ ID NO 5
<211> LENGTH: 405
<212> TYPE: DNA
<213> ORGANISM: Rattus norvegicus

<400> SEQUENCE: 5
atggacaggc ttacttcctc attcctactg ctgattgtcc ctgcatatgt cctgtctcag     60
gttactctga aagagtctgg ccctgggata ttgcagccct cccagaccct cagtctgact    120
tgcactttct ctgggttttc actgagcact tatggtatgg gtgtgggctg gattcgtcag    180
ccttcaggga agggtctgga gtggctggca aacatttggt gggatgatga aagtactac    240
aatccatctc tgaaaaaccg gctcacaatc tccaaggaca cctccaacaa ccaagcattc    300
ctcaagatca ccaatgtgga cactgcagat actgccacat actactgtgc tcggccttct    360
gcgtggggtt actggggcca aggagtcatg gtcacagtct cctca                    405

<210> SEQ ID NO 6
<211> LENGTH: 135
<212> TYPE: PRT
<213> ORGANISM: Rattus norvegicus

<400> SEQUENCE: 6

Met Asp Arg Leu Thr Ser Ser Phe Leu Leu Leu Ile Val Pro Ala Tyr
  1               5                  10                  15

Val Leu Ser Gln Val Thr Leu Lys Glu Ser Gly Pro Gly Ile Leu Gln
             20                  25                  30

Pro Ser Gln Thr Leu Ser Leu Thr Cys Thr Phe Ser Gly Phe Ser Leu
         35                  40                  45

Ser Thr Tyr Gly Met Gly Val Gly Trp Ile Arg Gln Pro Ser Gly Lys
 50                  55                  60

Gly Leu Glu Trp Leu Ala Asn Ile Trp Trp Asp Asp Lys Tyr Tyr
 65                  70                  75                  80

Asn Pro Ser Leu Lys Asn Arg Leu Thr Ile Ser Lys Asp Thr Ser Asn
                 85                  90                  95

Asn Gln Ala Phe Leu Lys Ile Thr Asn Val Asp Thr Ala Asp Thr Ala
             100                 105                 110

Thr Tyr Tyr Cys Ala Arg Pro Ser Ala Trp Gly Tyr Trp Gly Gln Gly
         115                 120                 125

Val Met Val Thr Val Ser Ser
    130                 135

<210> SEQ ID NO 7
<211> LENGTH: 396

```
<212> TYPE: DNA
<213> ORGANISM: Rattus norvegicus

<400> SEQUENCE: 7
atgatgattc ctgcccagtt cctgtctctg ctaatgctct ggatccagga agccggcgga    60
gatgttgtga tgacccagac accaccgtct ttgtcggttg ccattggaca atcagtctcc   120
atctcttgca agtcaagtca gagcctcgta tatagtgatg aaagacata tttgcattgg    180 ttattacaga gttctggccg gtctccgaag cgcctaatct atcaggtgtc taatctggac   240
tctggagtcc ctgacaggtt cagtggcact ggatcacaga agattttac acttaaaatc    300 agcagagtag aggctaagga tttgggagtt tattactgcg cgcaaactac acattttcct   360
ccgacgttcg gtggaggcac aagctggaa ttgaaa                              396

<210> SEQ ID NO 8
<211> LENGTH: 132
<212> TYPE: PRT
<213> ORGANISM: Rattus norvegicus

<400> SEQUENCE: 8

Met Met Ile Pro Ala Gln Phe Leu Ser Leu Leu Met Leu Trp Ile Gln
1               5                   10                  15

Glu Ala Gly Gly Asp Val Val Met Thr Gln Thr Pro Pro Ser Leu Ser
            20                  25                  30

Val Ala Ile Gly Gln Ser Val Ser Ile Ser Cys Lys Ser Ser Gln Ser
        35                  40                  45

Leu Val Tyr Ser Asp Gly Lys Thr Tyr Leu His Trp Leu Leu Gln Ser
    50                  55                  60

Ser Gly Arg Ser Pro Lys Arg Leu Ile Tyr Gln Val Ser Asn Leu Asp
65                  70                  75                  80

Ser Gly Val Pro Asp Arg Phe Ser Gly Thr Gly Ser Gln Lys Asp Phe
                85                  90                  95

Thr Leu Lys Ile Ser Arg Val Glu Ala Lys Asp Leu Gly Val Tyr Tyr
            100                 105                 110

Cys Ala Gln Thr Thr His Phe Pro Pro Thr Phe Gly Gly Gly Thr Lys
        115                 120                 125

Leu Glu Leu Lys
    130

<210> SEQ ID NO 9
<211> LENGTH: 999
<212> TYPE: DNA
<213> ORGANISM: Rattus norvegicus

<400> SEQUENCE: 9
gcccaaacaa cagcccatc tgtctatcca ctggctcctg gatgtggtga tacaaccagc     60
tccacggtga ctctgggatg cctggtcaag gctatttcc ctgagccagt caccgtgacc   120
tggaactctg gagccctgtc cagcgatgtg cacaccttc cagctgtcct gcagtctggg    180
ctctacactc tcaccagctc agtgacctcc agcacctggc ccagccagac cgtcacctgc   240
aacgtagccc accggccag cagcaccaag gtggacaaga agttgagcg cagaaatggc   300 ggcattggac acaaatgccc tacatgccct acatgtcaca aatgcccagt tcctgaactc   360
ttgggtggac catctgtctt catcttcccg ccaaagccca aggacatcct cttgatctcc   420
cagaacgcca aggtcacgtg tgtggtggtg gatgtgagcg aggaggagcc ggacgtccag   480
ttcagctggt ttgtgaacaa cgtagaagta cacacagctc agacacaacc ccgtgaggag   540
```

```
cagtacaaca gcaccttcag agtggtcagt gccctcccca tccagcacca ggactggatg      600
agcggcaagg agttcaaatg caaggtcaac aacaaagccc tcccaagccc catcgagaaa      660
accatctcaa acccaaagg gctagtcaga aaaccacagg tatacgtcat gggtccaccg       720
acagagcagt tgactgagca acggtcagt ttgacctgct tgacctcagg cttcctccct       780
aacgacatcg gtgtggagtg gaccagcaac gggcatatag aaaagaacta caagaacacc     840
gagccagtga tggactctga cggttctttc ttcatgtaca gcaagctcaa tgtggaaagg     900
agcaggtggg atagcagagc gcccttcgtc tgctccgtgg tccacgaggg tctgcacaat     960
caccacgtgg agaagagcat ctcccggcct ccgggtaaa                            999
```

<210> SEQ ID NO 10
<211> LENGTH: 333
<212> TYPE: PRT
<213> ORGANISM: Rattus norvegicus

<400> SEQUENCE: 10

```
Ala Gln Thr Thr Ala Pro Ser Val Tyr Pro Leu Ala Pro Gly Cys Gly
 1               5                  10                  15

Asp Thr Thr Ser Ser Thr Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Asp Val His Thr Phe Pro Ala Val Leu Gln Ser Gly Leu Tyr Thr Leu
    50                  55                  60

Thr Ser Ser Val Thr Ser Ser Thr Trp Pro Ser Gln Thr Val Thr Cys
65                  70                  75                  80

Asn Val Ala His Pro Ala Ser Ser Thr Lys Val Asp Lys Lys Val Glu
                85                  90                  95

Arg Arg Asn Gly Gly Ile Gly His Lys Cys Pro Thr Cys Pro Thr Cys
            100                 105                 110

His Lys Cys Pro Val Pro Glu Leu Leu Gly Gly Pro Ser Val Phe Ile
        115                 120                 125

Phe Pro Pro Lys Pro Lys Asp Ile Leu Leu Ile Ser Gln Asn Ala Lys
    130                 135                 140

Val Thr Cys Val Val Val Asp Val Ser Glu Glu Glu Pro Asp Val Gln
145                 150                 155                 160

Phe Ser Trp Phe Val Asn Asn Val Glu Val His Thr Ala Gln Thr Gln
                165                 170                 175

Pro Arg Glu Glu Gln Tyr Asn Ser Thr Phe Arg Val Val Ser Ala Leu
            180                 185                 190

Pro Ile Gln His Gln Asp Trp Met Ser Gly Lys Glu Phe Lys Cys Lys
        195                 200                 205

Val Asn Asn Lys Ala Leu Pro Ser Pro Ile Glu Lys Thr Ile Ser Lys
    210                 215                 220

Pro Lys Gly Leu Val Arg Lys Pro Gln Val Tyr Val Met Gly Pro Pro
225                 230                 235                 240

Thr Glu Gln Leu Thr Glu Gln Thr Val Ser Leu Thr Cys Leu Thr Ser
                245                 250                 255

Gly Phe Leu Pro Asn Asp Ile Gly Val Glu Trp Thr Ser Asn Gly His
            260                 265                 270

Ile Glu Lys Asn Tyr Lys Asn Thr Glu Pro Val Met Asp Ser Asp Gly
        275                 280                 285
```

```
Ser Phe Phe Met Tyr Ser Lys Leu Asn Val Glu Arg Ser Arg Trp Asp
        290                 295                 300

Ser Arg Ala Pro Phe Val Cys Ser Val Val His Glu Gly Leu His Asn
305                 310                 315                 320

His His Val Glu Lys Ser Ile Ser Arg Pro Pro Gly Lys
                325                 330

<210> SEQ ID NO 11
<211> LENGTH: 321
<212> TYPE: DNA
<213> ORGANISM: Rattus norvegicus

<400> SEQUENCE: 11
cgggctgatg ctgcaccaac tgtatccatc ttcccaccat ccatggaaca gttaacatct      60
ggaggtgcca cagtcgtgtg cttcgtgaac aacttctatc ccagagacat cagtgtcaag     120
tggaagattg atggcagtga acaacgagat ggtgtcctgg acagtgttac tgatcaggac     180
agcaaagaca gcacgtacag catgagcagc accctctcgt tgaccaaggt tgaatatgaa     240
aggcataacc tctatacctg tgaggttgtt cataagacat catcctcacc cgtcgtcaag     300
agcttcaaca ggaatgagtg t                                                321

<210> SEQ ID NO 12
<211> LENGTH: 107
<212> TYPE: PRT
<213> ORGANISM: Rattus norvegicus

<400> SEQUENCE: 12

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 13
<211> LENGTH: 1431
<212> TYPE: DNA
<213> ORGANISM: Artificial
<220> FEATURE:
<223> OTHER INFORMATION: Synthetic

<400> SEQUENCE: 13
atggaatgga gctggatctt tctcttcctc ctgtcaggaa ctacaggtgt ccactctgag      60
atccagctgc agcagtctgg acctgagctg gtgaagcctg gggcttcagt gaaggtttcc     120
tgcaaggctt ctggttactc attcactgac taccacatat actgggtgag gcagagccat     180
gaaaagagcc tagagtggat tggatatatt gatccttaca aggtggtac tacctacaac     240 cataatttca gggcaaggc ctcattgact gttgacaagt cctccagcac agccttcatg     300
catctcaaca gcctaacatc tgatgactct gcagtctatt actgtgcgag agaggctggc     360
```

| | |
|---|---|
| tataggtacg acaattactg gggccaaggg actctggtca ctgtctctgc agcccaaaca | 420 |
| acagccccat ctgtctatcc actggctcct ggatgtggtg atacaaccag ctccacggtg | 480 |
| actctgggat gcctggtcaa gggctatttc cctgagccag tcaccgtgac ctggaactct | 540 |
| ggagccctgt ccagcgatgt gcacaccttt ccagctgtcc tgcagtctgg gctctacact | 600 |
| ctcaccagct cagtgacctc cagcacctgg cccagccaga ccgtcacctg caacgtagcc | 660 |
| cacccggcca gcagcaccaa ggtggacaag aaagttgagc gcagaaatgg cggcattgga | 720 |
| cacaaatgcc ctacatgccc tacatgtcac aaatgcccag ttcctgaact cttgggtgga | 780 |
| ccatctgtct tcatcttccc gccaaagccc aaggacatcc tcttgatctc ccagaacgcc | 840 |
| aaggtcacgt gtgtggtggt ggatgtgagc gaggaggagc cggacgtcca gttcagctgg | 900 |
| tttgtgaaca acgtagaagt acacacagct cagacacaac cccgtgagga gcagtacaac | 960 |
| agcaccttca gagtggtcag tgccctcccc atccagcacc aggactggat gagcggcaag | 1020 |
| gagttcaaat gcaaggtcaa caacaaagcc ctcccaagcc catcgagaa aaccatctca | 1080 |
| aaacccaaag ggctagtcag aaaaccacag gtatacgtca tgggtccacc gacagagcag | 1140 |
| ttgactgagc aaacggtcag tttgacctgc ttgacctcag gcttcctccc taacgacatc | 1200 |
| ggtgtggagt ggaccagcaa cgggcatata gaaaagaact acaagaacac cgagccagtg | 1260 |
| atggactctg acggttcttt cttcatgtac agcaagctca atgtggaaag gagcaggtgg | 1320 |
| gatagcagag cgcccttcgt ctgctccgtg gtccacgagg gtctgcacaa tcaccacgtg | 1380 |
| gagaagagca tctcccggcc tccgggtaaa catcaccatc accatcatta g | 1431 |

<210> SEQ ID NO 14
<211> LENGTH: 735
<212> TYPE: DNA
<213> ORGANISM: Artificial
<220> FEATURE:
<223> OTHER INFORMATION: Synthetic

<400> SEQUENCE: 14

| | |
|---|---|
| atgaagttgc tgttaggct gttggtgctg atgttctgga ttcctgcttc cagcagtgat | 60 |
| gttgtgatga cccaaactcc actctccctg cctgtcagtc ttggagatca agcctccatt | 120 |
| tcttgcagat ctagtcagag ccttgtacac agtaatggaa acacctattt acattggtac | 180 |
| ctgcagaagg caggccagtc tccaaagctc ctgatctaca agtttccaa ccgatttttct | 240 |
| ggggtcccag acaggttcag tggcagtgga tcagggacag atttcacact caagatcagc | 300 |
| agagtggagg ctgaggatct gggagtttat ttctgctctc aaagtacaca tgttccgtgg | 360 |
| acgttcggtg gaggcaccaa gctggaaatc aaacggctg atgctgcacc aactgtatcc | 420 |
| atcttcccac catccatgga acagttaaca tctggaggtg ccacagtcgt gtgcttcgtg | 480 |
| aacaacttct atcccagaga catcagtgtc aagtggaaga ttgatggcag tgaacaacga | 540 |
| gatggtgtcc tggacagtgt tactgatcag gacagcaaag acagcacgta cagcatgagc | 600 |
| agcaccctct cgttgaccaa ggttgaatat gaaaggcata acctctatac ctgtgaggtt | 660 |
| gttcataaga catcatcctc acccgtcgtc aagagcttca acaggaatga gtgtcatcac | 720 |
| catcaccatc attag | 735 |

<210> SEQ ID NO 15
<211> LENGTH: 1425
<212> TYPE: DNA
<213> ORGANISM: Artificial
<220> FEATURE:

<223> OTHER INFORMATION: Synthetic

<400> SEQUENCE: 15

```
atggacaggc ttacttcctc attcctactg ctgattgtcc ctgcatatgt cctgtctcag      60
gttactctga aagagtctgg ccctgggata ttgcagccct cccagaccct cagtctgact     120
tgcactttct ctgggttttc actgagcact tatggtatgg gtgtgggctg gattcgtcag     180
ccttcaggga agggtctgga gtggctggca acatttggt gggatgatga taagtactac     240
aatccatctc tgaaaaaccg gctcacaatc tccaaggaca cctccaacaa ccaagcattc     300
ctcaagatca ccaatgtgga cactgcagat actgccacat actactgtgc tcggccttct     360
gcgtggggtt actggggcca aggagtcatg gtcacagtct cctcagccca acaacagcc      420
ccatctgtct atccactggc tcctggatgt ggtgatacaa ccagctccac ggtgactctg     480
ggatgcctgg tcaagggcta tttccctgag ccagtcaccg tgacctggaa ctctggagcc     540
ctgtccagcg atgtgcacac ctttccagct gtcctgcagt ctgggctcta cactctcacc     600
agctcagtga cctccagcac ctggcccagc cagaccgtca cctgcaacgt agcccacccg     660
gccagcagca ccaaggtgga caagaaagtt gagcgcagaa atggcggcat tggacacaaa     720
tgccctacat gccctacatg tcacaaatgc ccagttcctg aactcttggg tggaccatct     780
gtcttcatct cccgccaaaa gcccaaggac atcctcttga tctcccagaa cgccaaggtc     840
acgtgtgtgt ggtggatgt gagcgaggag gagccggacg tccagttcag ctggtttgtg     900
aacaacgtag aagtacacac agctcagaca caaccccgtg aggagcagta caacagcacc     960
ttcagagtgg tcagtgccct ccccatccag caccaggact ggatgagcgg caaggagttc    1020
aaatgcaagg tcaacaacaa agccctccca gccccatcg agaaaaccat ctcaaaaccc     1080
aaagggctag tcagaaaacc acaggtatac gtcatgggtc caccgacaga gcagttgact    1140
gagcaaacgg tcagtttgac ctgcttgacc tcaggcttcc tccctaacga catcggtgtg    1200
gagtggacca gcaacgggca tatagaaaag aactacaaga acaccgagcc agtgatggac    1260
tctgacggtt ctttcttcat gtacagcaag ctcaatgtgg aaaggagcag gtgggatagc    1320
agagcgccct tcgtctgctc cgtggtccac gagggtctgc acaatcacca cgtggagaag    1380
agcatctccc ggcctccggg taaacatcac catcaccatc attag                    1425
```

<210> SEQ ID NO 16
<211> LENGTH: 738
<212> TYPE: DNA
<213> ORGANISM: Artificial
<220> FEATURE:
<223> OTHER INFORMATION: Synthetic

<400> SEQUENCE: 16

```
atgatgattc ctgcccagtt cctgtctctg ctaatgctct ggatccagga agccggcgga      60
gatgttgtga tgacccagac caccacgtct tgtcggttg ccattggaca atcagtctcc     120
atctcttgca gtcaagtca gagcctcgta tatagtgatg gaaagacata tttgcattgg     180
ttattacaga gttctggccg gtctccgaag cgcctaatct atcaggtgtc taatctggac     240
tctggagtcc ctgacaggtt cagtggcact ggatcacaga agattttac acttaaaatc     300
agcagagtag aggctaagga tttgggagtt tattactgcg cgcaaactac acattttcct     360
ccgacgttcg gtggaggcac caagctggaa ttgaaacggg ctgatgctgc accaactgta     420
tccatcttcc caccatccat ggaacagtta acatctggag gtgccacagt cgtgtgcttc     480
gtgaacaact tctatcccag agacatcagt gtcaagtgga agattgatgg cagtgaacaa     540
```
cgagatggtg tcctggacag tgttactgat caggacagca aagacagcac gtacagcatg    600
agcagcaccc tctcgttgac caaggttgaa tatgaaaggc ataacctcta tacctgtgag    660
gttgttcata agacatcatc ctcacccgtc gtcaagagct tcaacaggaa tgagtgtcat    720
caccatcacc atcattag                                                 738

<210> SEQ ID NO 17
<211> LENGTH: 45
<212> TYPE: DNA
<213> ORGANISM: Artificial
<220> FEATURE:
<223> OTHER INFORMATION: primer

<400> SEQUENCE: 17
ctaatacgac tcactatagg gcaagcagtg gtatcaacgc agagt                    45

<210> SEQ ID NO 18
<211> LENGTH: 22
<212> TYPE: DNA
<213> ORGANISM: Artificial
<220> FEATURE:
<223> OTHER INFORMATION: primer

<400> SEQUENCE: 18
ctaatacgac tcactatagg gc                                             22

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
agggaaatar cccttgacca g                                              21

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
gcacctccag atgttaactg                                                20

<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21
tcctggatgt ggtgatacaa ccagc                                          25

<210> SEQ ID NO 22
<211> LENGTH: 26
<212> TYPE: DNA
<213> ORGANISM: Artificial
<220> FEATURE:
<223> OTHER INFORMATION: primer

<400> SEQUENCE: 22

-continued gggtgcttta tttacacaag ggaagg                                        26

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
atggacaggc ttacttcctc a                                            21

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
ggttgtatca ccacatccag                                              20

<210> SEQ ID NO 25
<211> LENGTH: 19
<212> TYPE: DNA
<213> ORGANISM: Artificial
<220> FEATURE:
<223> OTHER INFORMATION: primer

<400> SEQUENCE: 25
tttacccgga ggccgggag                                               19

<210> SEQ ID NO 26
<211> LENGTH: 34
<212> TYPE: DNA
<213> ORGANISM: Artificial
<220> FEATURE:
<223> OTHER INFORMATION: primer

<400> SEQUENCE: 26
ataacgcgat cgcatggaca ggcttacttc ctca                              34

<210> SEQ ID NO 27
<211> LENGTH: 40
<212> TYPE: DNA
<213> ORGANISM: Artificial
<220> FEATURE:
<223> OTHER INFORMATION: primer

<400> SEQUENCE: 27
ctaatgatgg tgatggtgat gtttacccgg aggccgggag                        40

<210> SEQ ID NO 28
<211> LENGTH: 22
<212> TYPE: DNA
<213> ORGANISM: Artificial
<220> FEATURE:
<223> OTHER INFORMATION: primer

<400> SEQUENCE: 28
atggaatgga gctggatctt tc                                           22

<210> SEQ ID NO 29
<211> LENGTH: 36
<212> TYPE: DNA
<213> ORGANISM: Artificial

```
<220> FEATURE:
<223> OTHER INFORMATION: primer

<400> SEQUENCE: 29
gggctgttgt ttgggctgca gagacagtga ccagag                          36

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
gcccaaacaa cagccccatc                                            20

<210> SEQ ID NO 31
<211> LENGTH: 35
<212> TYPE: DNA
<213> ORGANISM: Artificial
<220> FEATURE:
<223> OTHER INFORMATION: primer

<400> SEQUENCE: 31
ataacgcgat cgcatggaat ggagctggat ctttc                           35

<210> SEQ ID NO 32
<211> LENGTH: 25
<212> TYPE: DNA
<213> ORGANISM: Artificial
<220> FEATURE:
<223> OTHER INFORMATION: primer

<400> SEQUENCE: 32
aggcaccaag ctggaattga aacgg                                      25

<210> SEQ ID NO 33
<211> LENGTH: 25
<212> TYPE: DNA
<213> ORGANISM: Artificial
<220> FEATURE:
<223> OTHER INFORMATION: primer

<400> SEQUENCE: 33
gcaggtggca cctcaggacc tttgg                                      25

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
atgaagttgc ctgttaggct g                                          21

<210> SEQ ID NO 35
<211> LENGTH: 36
<212> TYPE: DNA
<213> ORGANISM: Artificial
<220> FEATURE:
<223> OTHER INFORMATION: primer

<400> SEQUENCE: 35
gtgcagcatc agcccgtttg atttccagct tggtgc                          36
```

<210> SEQ ID NO 36
<211> LENGTH: 21
<212> TYPE: DNA
<213> ORGANISM: Artificial
<220> FEATURE:
<223> OTHER INFORMATION: primer

<400> SEQUENCE: 36
atgatgattc ctgcccagtt c                                           21

<210> SEQ ID NO 37
<211> LENGTH: 35
<212> TYPE: DNA
<213> ORGANISM: Artificial
<220> FEATURE:
<223> OTHER INFORMATION: primer

<400> SEQUENCE: 37
gtgcagcatc agcccgtttc aattccagct tggtg                            35

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
cgggctgatg ctgcaccaac                                             20

<210> SEQ ID NO 39
<211> LENGTH: 21
<212> TYPE: DNA
<213> ORGANISM: Artificial
<220> FEATURE:
<223> OTHER INFORMATION: primer

<400> SEQUENCE: 39
acactcattc ctgttgaagc t                                           21

<210> SEQ ID NO 40
<211> LENGTH: 34
<212> TYPE: DNA
<213> ORGANISM: Artificial
<220> FEATURE:
<223> OTHER INFORMATION: primer

<400> SEQUENCE: 40
ataacgcgat cgcatgaagt tgcctgttag gctg                             34

<210> SEQ ID NO 41
<211> LENGTH: 42
<212> TYPE: DNA
<213> ORGANISM: Artificial
<220> FEATURE:
<223> OTHER INFORMATION: primer

<400> SEQUENCE: 41
ctaatgatgg tgatggtgat gacactcatt cctgttgaag ct                    42

<210> SEQ ID NO 42
<211> LENGTH: 34
<212> TYPE: DNA
<213> ORGANISM: Artificial
<220> FEATURE:
<223> OTHER INFORMATION: primer -continued

```
<400> SEQUENCE: 42
ataacgcgat cgcatgatga ttcctgccca gttc                              34

<210> SEQ ID NO 43
<211> LENGTH: 33
<212> TYPE: DNA
<213> ORGANISM: Artificial
<220> FEATURE:
<223> OTHER INFORMATION: primer

<400> SEQUENCE: 43
ccccgaattc accatggaat ggagctggat ctt                               33

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
cccctctaga ctaatgatgg tgatggtgat                                   30

<210> SEQ ID NO 45
<211> LENGTH: 33
<212> TYPE: DNA
<213> ORGANISM: Artificial
<220> FEATURE:
<223> OTHER INFORMATION: primer

<400> SEQUENCE: 45
ccccgaattc accatgaagt tgcctgttag gct                               33

<210> SEQ ID NO 46
<211> LENGTH: 33
<212> TYPE: DNA
<213> ORGANISM: Artificial
<220> FEATURE:
<223> OTHER INFORMATION: primer

<400> SEQUENCE: 46
ccccgaattc accatggaca ggcttacttc ctc                               33

<210> SEQ ID NO 47
<211> LENGTH: 33
<212> TYPE: DNA
<213> ORGANISM: Artificial
<220> FEATURE:
<223> OTHER INFORMATION: primer

<400> SEQUENCE: 47
ccccgaattc accatgatga ttcctgccca gtt                               33

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
ccccgaattc gagatccagc tgcagcagtc                                   30

<210> SEQ ID NO 49
```

```
<211> LENGTH: 30
<212> TYPE: DNA
<213> ORGANISM: Artificial
<220> FEATURE:
<223> OTHER INFORMATION: primer

<400> SEQUENCE: 49
ccccgaattc gatgttgtga tgacccaaac                                    30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
ccccgaattc caggttactc tgaaagagtc                                    30

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
ccccgaattc gatgttgtga tgacccagac                                    30
```